United States Patent
Su et al.

(10) Patent No.: US 9,707,396 B2
(45) Date of Patent: Jul. 18, 2017

(54) CORTICAL POTENTIAL MONITORING

(71) Applicant: Medtronic, Inc., Minneapolis, MN (US)

(72) Inventors: Xin Su, Plymouth, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 14/063,919

(22) Filed: Oct. 25, 2013

(65) Prior Publication Data

US 2014/0378941 A1 Dec. 25, 2014

Related U.S. Application Data

(60) Provisional application No. 61/838,060, filed on Jun. 21, 2013.

(51) Int. Cl.
*A61N 1/36* (2006.01)
*A61B 5/0484* (2006.01)
(Continued)

(52) U.S. Cl.
CPC ........ *A61N 1/36139* (2013.01); *A61B 5/0484* (2013.01); *A61B 5/4255* (2013.01);
(Continued)

(58) Field of Classification Search
CPC ............ A61N 1/36139; A61N 1/36007; A61N 1/37241; A61B 5/0484; A61B 5/4255; A61M 5/1723
(Continued)

(56) References Cited

U.S. PATENT DOCUMENTS 7,983,757 B2 7/2011 Miyazawa et al.
8,126,567 B2 2/2012 Gerber et al.
(Continued)

OTHER PUBLICATIONS

Badr, et al., "Cortical evoked potentials obtained after stimulation of the lower urinary tract," J. Urol, Feb. 1984, pp. 306-309.
(Continued)

*Primary Examiner* — Christopher D Koharski
*Assistant Examiner* — Jeremiah Kimball
(74) *Attorney, Agent, or Firm* — Shumaker & Sieffert, P.A.

(57) ABSTRACT

Techniques, devices, and systems may include screening effective therapies using cortical evoked potentials. In one example, a system may be configured to receive a first sensed cortical evoked potential of a patient that occurred in response to an induced sensation at an anatomical region different from a brain region of the patient and receive a second sensed cortical evoked potential that occurred in response to electrical stimulation delivered to one or more nerves associated with the anatomical region. The electrical stimulation may be at least partially defined by a set of therapy parameter values. The system may also compare a first value of a characteristic of the first sensed cortical evoked potential to a second value of the characteristic of the second sensed cortical evoked potential and determine, based on the comparison, efficacy of a therapy configured to treat a condition associated with the anatomical region.

23 Claims, 10 Drawing Sheets

(51) Int. Cl.
*A61M 5/172* (2006.01)
*A61N 1/372* (2006.01)
*A61B 5/00* (2006.01)

(52) U.S. Cl.
CPC ....... *A61M 5/1723* (2013.01); *A61N 1/36007* (2013.01); *A61N 1/37241* (2013.01)

(58) Field of Classification Search
USPC .................................. 607/115, 41; 600/544
See application file for complete search history.

(56) References Cited

U.S. PATENT DOCUMENTS

| 8,185,207 | B2 | 5/2012 | Molnar et al. | |
|---|---|---|---|---|
| 2006/0235472 | A1* | 10/2006 | Goetz | A61N 1/36135 607/2 |
| 2007/0255346 | A1* | 11/2007 | Rondoni | A61N 1/36071 607/59 |
| 2008/0300449 | A1* | 12/2008 | Gerber | A61N 1/36007 600/30 |
| 2009/0112281 | A1* | 4/2009 | Miyazawa | A61N 1/36071 607/46 |
| 2010/0100153 | A1* | 4/2010 | Carlson | A61N 1/0529 607/45 |

OTHER PUBLICATIONS

Braun, et al., "Alterations of Cortical Electrical Activity in Patients with Sacral Neuromodulator," European Urology, Jan. 8, 2002, 6 pp.

Gerstenberg, et al., "Urinary cerebral-evoked potentials mediated through urethral sensory nerves—a preliminary report," Female Incontinence, Feb. 1981, pp. 141-143.

Giani, et al., "The Effect of Sacral Nerve Modulation on Cerebral Evoked Potential Latency in Fecal Incontinence and Constipation," Annals of Surgery, vol. 254, No. 1, Jul. 2011, pp. 90-96.

Hansen, et al., "Cerebral evoked potentials after stimulation of the posterior urethra in man.," Electroencephalogr Clin Neurophsiol, Jan. 1990, pp. 52-58.

Liao, et al., Effect of sacral-root stimulation on the motor cortex in patients with idiopathic overactive bladder syndrome, Neurophysiologie Clinique/Clinical Neurophysiology, Feb. 2008, pp. 39-43.

Malaguti, et al., "Neurophysiological evidence may predict the outcome of sacral neuromodulation," The Journal of Urology, vol. 170, Dec. 2003, pp. 2323-2326.

Mazo, et al., "The Role of somatosensory evoked potentials in prognosis of efficacy of tibial neuromodulation in patients with hyperactive urinary bladder," Sep.-Oct. 2005, [English Abstract on p. 52], pp. 49-52.

Wu, et al., "Somatosensory evoked potential from S1 nerve root stimulation," Eur Spine, Oct. 2011, pp. 1613-1619.

* cited by examiner

CORTICAL POTENTIAL MONITORING

This application claims the benefit of U.S. Provisional Patent Application No. 61/838,060, to Su, filed Jun. 21, 2013, and entitled "CORTICAL POTENTIAL MONITORING," which is incorporated herein by reference in its entirety.

TECHNICAL FIELD

The disclosure relates to medical devices and, more particularly, medical devices for sensing brain signals for monitoring and/or treating a patient condition.

BACKGROUND

Fecal incontinence, or an inability to control defecation function, is a problem that may afflict people of all ages, genders, and races. Various muscles, nerves, organs and conduits within the pelvic floor may cooperate to collect, store and release fecal matter. A variety of disorders may compromise the ability of a person to control rectal voiding, and contribute to fecal incontinence. Many of the disorders may be associated with aging, injury or illness.

In some cases, fecal incontinence can be attributed to inadequate sensation in the rectum that prevents a person from controlling voiding events. This inadequate sensation may be attributable to a dysfunction of the nervous system. In other cases, a person may have a weakened sphincter muscle or other muscular disorder that prevents adequate control of bowel voiding. These and other conditions may result in fecal incontinence. Other pelvic floor disorders (e.g., urinary incontinence) may include similar deficiencies that result in abnormal function.

SUMMARY

Techniques, devices, and systems for screening effective therapies using cortical evoked potentials are described. Stimulation induced upon an anatomical region of the pelvic floor (e.g., a patient's bowel) may cause cortical evoked potentials from the patient's brain. These cortical evoked potentials may be referred to as baseline response values. Electrical stimulation of a nerve, such as the second sacral (S2) nerve may also elicit cortical evoked potentials at the same or similar location of the patient's brain. However, the values of a characteristic of these cortical evoked potentials may be different from the baseline values of the characteristic of the cortical evoked potential caused by the induced stimulation of the anatomical region. In this way, one or more characteristics of a cortical evoked potential evoked in response to delivery of therapy to the patient may be a biomarker for the patient responsiveness to the therapy of delivery, and, in some examples, a biomarker for efficacious therapy delivery. The one or more characteristics of the cortical evoked potential may include, for example, an amplitude of the evoked potential, a duration of the evoked potential, and a latency between stimulation delivery and the evoked potential.

A system may determine that a therapy (e.g., electrical stimulation therapy or pharmaceutical delivery therapy) to treat a condition (e.g., fecal incontinence) of the anatomical region (e.g., the bowel) is effective when the value of the characteristic of the cortical evoked potential responsive to the therapy delivery (e.g., therapy delivery that modulates activity of a nerve) is greater than the baseline value. In some examples, a system may be configured to select specific therapy parameter values for electrical stimulation therapy or another therapy, such as pharmaceutical agent delivery therapy (e.g., via an automated pump or manually administered), based on differential between values of the cortical evoked potentials from the electrical stimulation and the baseline values. This screening tool may be used to diagnose a patient condition, monitor disease progression, select therapy parameter values for electrical stimulation therapy or another therapy, and/or provide feedback for closed-loop electrical stimulation therapy.

In one aspect, the disclosure is directed to a method that includes receiving a first sensed cortical evoked potential of a patient that occurred in response to an induced sensation at an anatomical region of the patient different from a brain region of the patient, receiving a second sensed cortical evoked potential that occurred in response to electrical stimulation delivered to one or more nerves associated with the anatomical region, wherein the electrical stimulation is at least partially defined by a set of therapy parameter values, comparing, by one or more processors, a first value of a characteristic of the first sensed cortical evoked potential to a second value of the characteristic of the second sensed cortical evoked potential, and determining, based on the comparison and by the one or more processors, efficacy of a therapy configured to treat a condition associated with the anatomical region.

In another aspect, the disclosure is directed to a system that includes one or more processors configured to receive a first sensed cortical evoked potential of a patient that occurred in response to an induced sensation at an anatomical region of the patient different from a brain region of the patient, receive a second sensed cortical evoked potential that occurred in response to electrical stimulation delivered to one or more nerves associated with the anatomical region, wherein the electrical stimulation is at least partially defined by a set of therapy parameter values, compare a first value of a characteristic of the first sensed cortical evoked potential to a second value of the characteristic of the second sensed cortical evoked potential, and determine, based on the comparison, efficacy of a therapy configured to treat a condition associated with the anatomical region.

In another aspect, the disclosure is directed to a system that includes means for receiving a first sensed cortical evoked potential of a patient that occurred in response to an induced sensation at an anatomical region of the patient different from a brain region of the patient, means for receiving a second sensed cortical evoked potential that occurred in response to electrical stimulation delivered to one or more nerves associated with the anatomical region, wherein the electrical stimulation is at least partially defined by a set of therapy parameter values, means for comparing a first value of a characteristic of the first sensed cortical evoked potential to a second value of the characteristic of the second sensed cortical evoked potential, and means for determining, based on the comparison, efficacy of a therapy configured to treat a condition associated with the anatomical region.

In another aspect, the disclosure is directed to a computer-readable storage medium that includes one or more instructions that, when executed by one or more processors, cause the one or more processors to receive a first sensed cortical evoked potential of a patient that occurred in response to an induced sensation at an anatomical region of the patient different from a brain region of the patient, receive a second sensed cortical evoked potential that occurred in response to electrical stimulation delivered to one or more nerves associated with the anatomical region, wherein the electrical stimulation is at least partially defined by a set of therapy parameter values, compare a first value of a characteristic of the first sensed cortical evoked potential to a second value of the characteristic of the second sensed cortical evoked potential, and determine, based on the comparison, efficacy of a therapy configured to treat a condition associated with the anatomical region.

The details of one or more aspects of the disclosure are set forth in the accompanying drawings and the description below. Other features, objects, and advantages of the examples of the disclosure will be apparent from the description and drawings, and from the claims.

DETAILED DESCRIPTION

Figure 1:
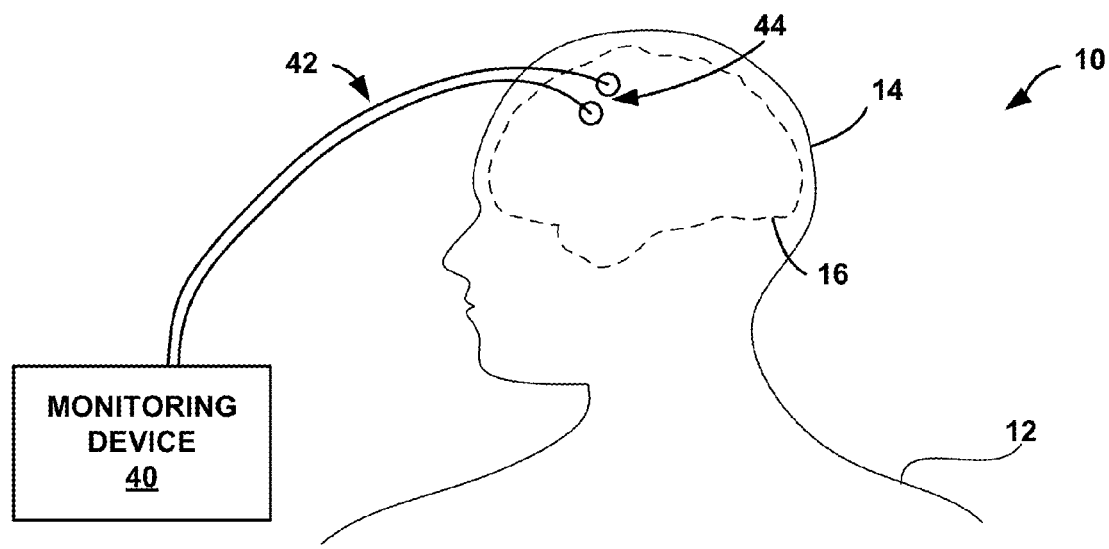
FIG. 1 is a conceptual diagram illustrating an example system configured to control delivery of electrical stimulation and sense cortical evoked potentials to screen for effective therapy to treat a bowel related condition of a patient.
Figure 1:
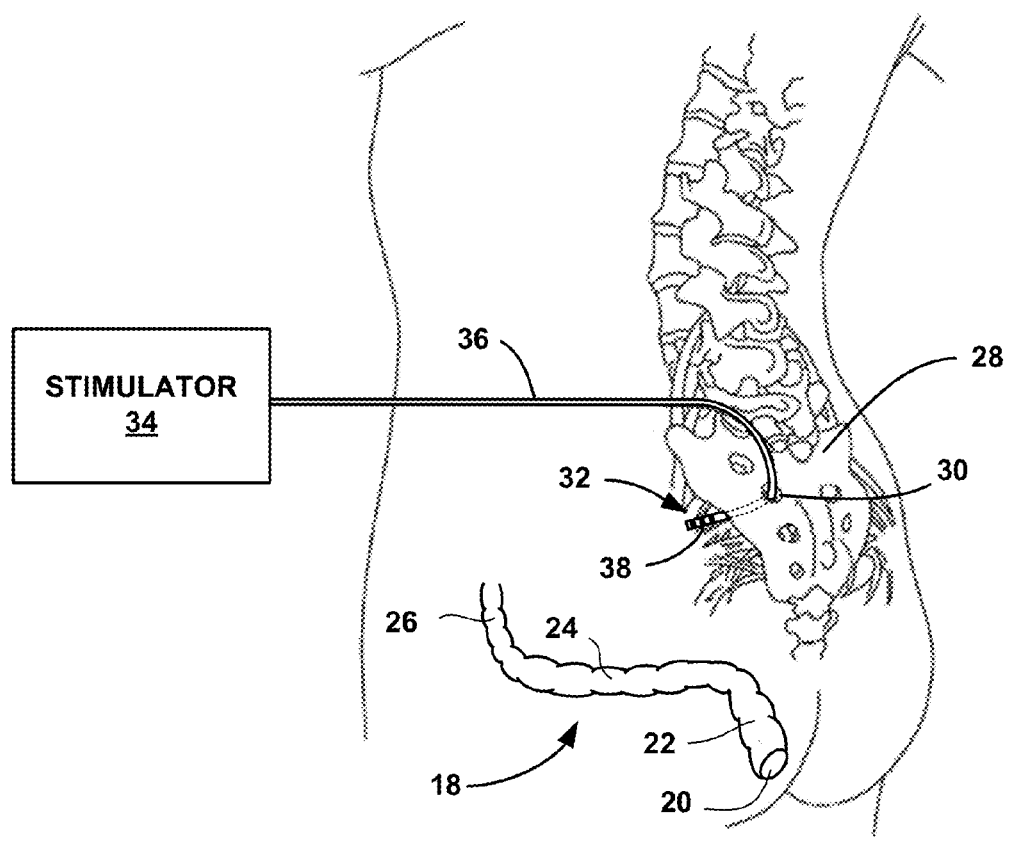

This disclosure describes techniques, devices, and systems for identifying potentially effective therapies based on cortical evoked potentials. Pelvic floor conditions and disorders may be caused by a variety of factors such as age, illness, or injury. The symptoms of pelvic floor disorders may be caused by weakness of one or more muscles, compromised tissues, and/or disrupted or damaged neurological pathways (e.g., nerves). For any of these reasons, a patient may lose control or sensation of various pelvic floor activities.

In one example, a patient may suffer from fecal incontinence. Fecal incontinence may refer to a condition of involuntary loss of fecal matter, and may include urge incontinence, stress incontinence, or both stress and urge incontinence, which may be referred to as mixed incontinence. As used in this disclosure, the term "fecal incontinence" includes disorders in which fecal matter is voided (i.e., defecation) when not desired, such as stress or urge incontinence, and disorders in which fecal voiding does not occur as desired, such as irritable bowel syndrome.

One type of therapy for treating fecal incontinence may include delivery of electrical stimulation therapy. For example, delivery of electrical stimulation from an implantable medical device to nerves in the pelvic floor, such as one or more of the sacral nerves (e.g. the second sacral nerve) may provide an effective therapy for fecal incontinence for some patients. Electrical stimulation of the sacral nerve may modulate afferent nerve activities to restore desired voiding function. In addition, electrical stimulation of the nerves innervating pelvic floor muscles may strengthen pelvic floor muscle and promote fecal continence. In some examples, pharmaceutical therapy may additionally or alternatively be provided to the patient. Similar to fecal incontinence, urinary incontinence or other pelvic floor disorders (e.g., sexual dysfunction) may also result from a lack of voluntary control and may be treated with electrical stimulation, pharmaceuticals, or other therapies.

However, screening patients for responsiveness to electrical stimulation or pharmaceutical therapy, effective therapy, or adjusting therapy over time can provide some challenges. For example, electrical stimulation may be initially delivered on a trial basis over several hours, days, or weeks. The trial electrical stimulation may be delivered to one or more nerves or directly to appropriate muscles (e.g., a sphincter), but the efficacy (or response of the patient to the electrical stimulation) of such stimulation may not be evident until the patient has experienced one or more voiding cycles. In other words, the patient may need to evaluate the therapy over a relatively long period of time before the therapy can be identified as reducing or eliminating incontinence symptoms. Moreover, once a therapy is identified as potentially effective, the patient may need to iteratively try different therapy parameter values, or different sets of therapy parameters, to find the most effective therapy for treating the patient's condition. This process can take days, weeks, or even months.

Techniques described in this disclosure utilize sensed cortical evoked potentials from the brain of the patient to more quickly identify therapies, or even specific therapy parameter values, that may likely reduce or eliminate the symptoms of the patient. A cortical evoked potential can be or include, for example, a response in a cortex of a brain of a patient evoked by the delivery of therapy (e.g., electrical stimulation or pharmaceutical agent delivery therapy). A cortical evoked potential can be indicated by, for example, a sensed electrical brain signal (e.g., electroencephalography (EEG) or electrocorticogram (ECoG)). Sensations or stimulation occurring at a target anatomical region associated with the patient's condition (e.g., a rectum associated with fecal incontinence) can elicit cortical evoked potentials. These cortical evoked potentials caused by sensations in the bowel (e.g., stool, inserted object, or electrical stimulus) may indicate a neural pathway for therapy and may be used as a baseline indication of cortex location in the brain of the patient for the cortical evoked potentials that may be a biomarker for a responsiveness of the patient to therapy delivery.

A system may apply electrical stimulation to a nerve, such as a sacral nerve, in an attempt to elicit cortical evoked potentials at the same cortex location as the baseline. A comparison of the cortical evoked potentials (e.g., sensed via EEG) to the baseline may be indicative of whether or not the patient will respond to electrical stimulation therapy (or other therapy) and, in some examples, whether electrical stimulation will be effective at treating the condition of the patient. For example, if electrical stimulation delivered to the nerve elicits cortical evoked potentials greater than the baseline potentials, the electrical stimulation that was delivered may be effective at treating the condition related to the anatomical. In some examples, the difference between the cortical evoked potentials and the baseline potentials may need to be greater than an efficacy threshold to indicate that the patient may respond to the therapy and, in some examples, to indicate that the electrical stimulation may be effective in reducing or eliminating the symptoms of the patient's condition. When comparing cortical evoked potentials, one or more characteristics of the cortical evoked potentials may be compared. In other words, comparison of cortical evoked potentials may include comparing respective values of a common characteristic that at least partially describes the respective potentials.

In other examples, a system may evaluate, or screen, a plurality of different therapy parameters sets to identify effective electrical stimulation to provide to the patient. For example, the system may iteratively deliver electrical stimulation defined by a respective set of therapy parameter values and monitor the resulting sensed cortical evoked potentials. The system may select the therapy parameter set that evoked a cortical potential that exhibited the relatively largest difference with the baseline potential. In this way, the relatively largest difference between the resulting sensed cortical evoked potentials and the baseline potentials (e.g., between the characteristics of the potentials) may be used as a guideline for selecting an efficacious therapy parameter set for a patient.

In some examples, the techniques described herein may be used to identify an effective therapy in a relatively short timeframe (e.g., within ten minutes in some cases) of beginning delivery of electrical stimulation. For example, the cortical evoked potentials may in some instances be sensed within ten minutes after the beginning electrical stimulation delivery. Thus, in some examples, sensing and comparing cortical evoked potentials may reduce or eliminate the need to evaluate potential therapies by waiting for voiding events to occur.

As described herein, in some examples, cortical evoked potentials may be used to determine potentially efficacious therapies for a patient. In addition, in some examples, a system may control therapy delivery based on monitored cortical evoked potentials (e.g. in a closed-loop or pseudo-closed-loop manner). For example, a system may monitor cortical evoked potentials during therapy and use the cortical evoked potentials as feedback to control subsequent electrical stimulation therapy. For example, in response to detecting cortical evoked potentials above a threshold, a medical device (e.g., an implantable medical device (IMD)) may reduce or cease stimulation to conserve power and/or reduce the likelihood of accommodation. As another example, a medical device may adjust one or more therapy parameter values that define the electrical stimulation in response to detecting changes to the sensed cortical evoked potentials. In any case, cortical evoked potentials may be monitored for feedback regarding the status or treatment of a target anatomical region instead of directly monitoring the anatomical region with a sensor at or adjacent to the anatomical region.

Although the techniques are primarily described in this disclosure for managing fecal incontinence, the techniques may also be applied to manage urinary incontinence. In urinary incontinence examples, baseline cortical evoked potentials may be established with sensations or stimulation to the urethra, urinary sphincters, or bladder and electrical stimulation may be delivered to different sacral nerve (e.g., the third sacral nerve). Similar techniques with respect to fecal incontinence may be used to identify potentially effective therapy to treat urinary incontinence. In addition, the techniques described herein may also be applicable to monitoring and/or treating other pelvic floor disorders (e.g., sexual dysfunction), pain, or any other conditions. A relationship between cortical potentials and a particular anatomical region of interest for therapy delivery may be established and then such cortical potentials may be used to determine whether a patient will respond to the therapy delivery, whether a particular set of therapy parameter values is efficacious, to control therapy delivery, or for any other technique described herein.

FIG. 1 is a conceptual diagram illustrating example system 10 configured to control delivery of electrical stimulation and sense cortical evoked potentials to screen for effective therapy to treat a bowel related condition of patient 12. As shown in FIG. 1, system 10 includes stimulator 34 (e.g., an electrical stimulator) coupled to medical lead 36 carrying electrodes 38 near a distal end of lead 36. Lead 36 may be a temporary percutaneous lead when stimulator 34 is an external trial stimulator or a stimulator located external to patient 12. In other examples, lead 36 may be fully implantable and connected to a lead extension (not shown) passing through the skin and coupled to stimulator 34. Stimulator 34 may deliver electrical stimulation at least partially defined by a set of therapy parameter values (e.g., current amplitude, voltage amplitude, pulse width, pulse frequency, and electrode combination). Although a single lead 36 is shown, two or more leads may be used in other examples.

System 10 also includes monitoring device 40 (e.g., a sensing device) coupled to external leads 42. Each of leads 42 is coupled to a respective one of surface electrodes 44. Surface electrodes 44 may be adhered or otherwise attached to skin of head 14. Surface electrodes 44 may be configured to sense cortical evoked potentials generated in the cortex of brain 16 of patient 12. The region of brain 16 from which electrodes 44 may sense cortical evoked potentials may include a portion of the cortex. In some examples, electrodes 44 may be positioned with respect to this portion of the cortex that may be known to be associated with portions of intestines 18, such as rectum 22. For example, electrodes 44 may be repositioned until an appropriate response to electrical stimulation of an anatomical region of interest of patient 12 (as discussed below) is achieved, or system 10 can include a plurality of electrodes (e.g., patient 12 may wear a cap that includes a plurality of electrodes positioned proximate to different areas of brain 16) and the electrodes from the plurality of electrodes that are positioned with respect to the portion of the cortex that may be known to be associated with portions of intestines 18 may be identified.

Although only two electrodes 44 are shown, system 10 may include three or more electrodes in other examples. In addition, electrodes 44 may be implantable or at least partially implantable in other examples. For example, leads 42 may be transcutaneous or electrodes 44 may be part of a fully implantable device for sensing and monitoring cortical evoked potentials from brain 16. Although monitoring device 40 and stimulator 34 are shown as separate devices, monitoring device 40 and stimulator 34 may be configured as part of a single device configured to deliver electrical stimulation and sense cortical evoked potentials.

Patient 12 includes intestines 18 that may be subject a condition such as fecal incontinence. Intestines 18 may include descending colon 26, sigmoid colon 24, rectum 22 and anus 20. During normal, or healthy, function of intestines 18, sigmoid colon 24, and rectum 22 are depicted such that their positions relative to one another form a "valve" or "fold" that prevents fecal matter from entering rectum 22. During a fecal voiding event, however, sigmoid colon 24 and rectum 22 may shift from the illustrated positions to positions that open the valve or fold thereby allowing fecal matter in sigmoid colon 24 to pass to rectum 22 and exit anus 20. When fecal matter is present in sigmoid colon 24 or rectum 22, patient 12 may typically recognize the sensation and take action (e.g., prevent fecal voiding or voluntarily void the fecal matter). However, for a patient with fecal incontinence, patient 12 may not recognize the sensation of fecal matter or be capable of voluntarily controlling the need to void.

Although fecal incontinence may be caused by muscular or neurological dysfunction, sensations and stimulation of pelvic floor nerves and/or sensed cortical evoked potentials may still be useful for identifying therapies that may be effective in treating the condition of patient 12. Sensed cortical evoked potentials may be used as an indicator, or biomarker, for determining one or more therapies that may be effective in treating the fecal incontinence of patient 12. Cortical evoked potentials may be indicative of sensations, stimulations, or actions occurring are various anatomical regions of the body. Each anatomical region may be associated with one or more respective locations of the cerebral cortex. For example, an anatomical region may be associated with a sensory area of the cerebral cortex and/or a motor area of the cerebral cortex. These sensory areas may or may not be located in the same region of the cerebral cortex as a corresponding motor area. Sensations at an anatomical region may thus result, or elicit, cortical evoked potentials at the respective sensory area of the cerebral cortex. Since an area of the cerebral cortex is associated with an anatomical region, sensing cortical evoked potentials at that area of the cerebral cortex may indicate activity of the anatomical region whether or not the activity occurred at the anatomical region or one or more nerves innervating the anatomical region.

As described herein, cortical evoked potentials may be used to identify electrical stimulation locations (e.g., tissues for receiving stimulation) and/or therapy parameter values that may alleviate one or more symptoms of a target anatomical region (also referred to herein as an anatomical region of interest). In the example of FIG. 1 related to fecal incontinence, the target anatomical region may include rectum 22. In order to find the region of brain 16 from which cortical evoked potentials occur from rectum 22 and generate a baseline for the cortical evoked potentials, a sensation must first be provided to rectum 22. This sensation may be induced in different ways. In one example, feces within rectum 22 may be sufficient to elicit cortical evoked potentials associated with rectum 22. A clinician may examine patient 12 to ensure that feces are in rectum 22 or patient 12 may be able to indicate when feces are present (e.g., prior to a voiding event). In another example, an object may be inserted through anus 20 and into rectum 22 to elicit cortical evoked potentials. The object may be a saline filled balloon, suppository, fluid, or even clinician palpation of rectum 22. In other examples, electrical stimulation may be delivered to rectum 22 (e.g., stimulation provided by stimulator 34).

In response to the induced sensation to rectum 22, monitoring device 40 may sense cortical evoked potentials at one or more regions of brain 16, which may be cortical potentials evoked in response to the induced sensation to rectum 22. The cortical evoked potentials may occur immediately or after a few minutes of time. Although the clinician may know by experience where to place electrodes 44, the clinician may still place electrodes 44 at multiple different locations, as indicated above, on head 14 in order to identify the location of the cerebral cortex that is associated with rectum 22. The target region of brain 16 may be the location at which monitoring device 40 senses increased cortical evoked potentials in response to the sensations induced in rectum 22. The location of electrodes 44 shown in FIG. 1 is one example location, but electrodes 44 (or any number of electrodes) may be placed at any other location or locations on head 14 and/or brain 16.

Monitoring device 40 may thus receive the sensed cortical evoked potentials of patient 12 that occurred in response to the induced sensation at the anatomical region of rectum 22. These cortical evoked potentials may be used as baseline potentials, or potentials that indicate typical patient 12 function without electrical stimulation therapy or other therapy. The sensed cortical evoked potentials may be stored as a raw signal such as amplitude over time or as one or more processed characteristics that represent aspects of the cortical evoked potentials. Example characteristics may include amplitude of the evoked potential, frequency of the evoked potentials, a power spectral density or spectrogram of the evoked potentials, a duration of the evoked potential, and a latency between stimulation delivery and the evoked potential. Values of one or more of these characteristics may be calculated and stored to represent the cortical evoked potentials sensed over time. The characteristic values stored as the baseline may be used to evaluate subsequent cortical evoked potentials sensed from electrical stimulation.

Stimulator 34 may also include a therapy delivery module and/or other components configured to deliver, via lead 36 and one or more electrodes 38, electrical stimulation to second sacral nerve 32 (i.e., S2) or other nerve that may potentially provide therapy to control the fecal incontinence of patient 12. In the example shown in FIG. 1, the distal end of lead 36 is inserted into sacral foramen 30 of sacrum 28. Since second sacral nerve 32 may be known to innervate portions of intestines 18 such as rectum 22, electrodes 38 may be implanted adjacent to second sacral nerve 32 to evaluate the efficacy of therapy delivered to this site. In this manner, the second sacral nerve 32 may be associated with the anatomical regions of intestines 18 and rectum 22. A nerve or nerves which innervate or otherwise carry impulses to or away from an anatomical region may be referred to as a nerve associated with the anatomical region. In other examples, stimulation of second sacral nerve 32 may be performed using electrodes external of the pelvic floor either subcutaneously implanted or placed on the external surface of the skin. However, these other locations may not be sufficiently precise to evaluate stimulation therapy. In some examples, stimulation may be delivered to second sacral nerve 32 and additional nerves adjacent to the sacral nerve. For example, stimulation may be delivered to both S2 and S3 nerves.

In some examples, a clinician may use the sensed cortical evoked potentials to find target nerves or other target therapy delivery sites that may, when stimulated, provide relief to the condition of the target anatomical region. For example, the clinician may iteratively stimulate at a first tissue location (e.g., a first nerve), monitor any cortical evoked potentials, move to a second tissue location, and repeat until one or more tissue locations have been identified with cortical evoked potentials sensed at the same location of the patient's brain as the baseline cortical evoked potentials were sensed. In this manner, system 10 may be used to screen different stimulation sites for effective therapy locations based on a comparison of cortical evoked potential locations for the different stimulation sites and the target anatomical region.

Stimulator 34 may be configured to deliver electrical stimulation to second sacral nerve 32 according to a selected set of stimulation therapy parameter values. This set of therapy parameter values may at least partially define the electrical stimulation and include parameter values for one or more therapy parameters such as current amplitude, voltage amplitude, pulse width, pulse frequency, waveshape (in examples that include continuous waveform delivery) and electrode combinations. The set of therapy parameter values may be selected according to clinician experience, patient condition, or any other circumstances. Subsequent to delivery of the electrical stimulation to sacral nerve 32, monitoring device 40 may sense cortical evoked potentials from a region of brain 16 that indicate a response to the delivered stimulation. Monitoring device 40 may sense the cortical evoked potentials over a period of time to look for changes in amplitude or some other characteristic to the sensed cortical evoked potentials that may be indicative of effective therapy.

Monitoring device 40 may thus be configured to receive the sensed cortical evoked potentials that occurred in response to the electrical stimulation delivered to second sacral nerve 32 associated with rectum 22. Monitoring device 40 may process the received cortical evoked potentials and determine values for one or more characteristics that represent the cortical evoked potentials. In addition, monitoring device 40 may be configured to compare the value of the characteristic of the baseline cortical evoked potential to the value of the characteristic of the sensed cortical evoked potential from the electrical stimulation to nerve 32. Based on this comparison, monitoring device 40 may be configured to determine the efficacy of the therapy configured to treat fecal incontinence associated with the anatomical region of rectum 22.

Monitoring device 40 may utilize one or more sensing modalities to sense the cortical evoked potentials from brain 16. The sensing modality may be noninvasive in one example. In one example, monitoring device 40 may use electrodes 44 and electroencephalography to generate an EEG of the cortical evoked potentials. In another example, monitoring device 40 may be configured to use mageneto-encephalography to generate a magenetoencephalogram (MEG) to sense the cortical evoked potential from brain 16. In an alternative example, monitoring device 40 may be configured to sense the cortical evoked potentials using functional magnetic resonance imaging (fMRI). Other example techniques for sensing or capturing cortical evoked potentials may include positron emission tomography (PET), or direct recording by electrodes. These and other examples are contemplated to sense cortical evoked potentials used to determine the efficacy of stimulation.

In one example, monitoring device 40 may determine or indicate that electrical stimulation therapy will be (or is predicted to be) effective based on the comparison of cortical evoked potentials to the baseline. Monitoring device 40 may be configured to determine that a difference between the values of a characteristic of the cortical evoked potentials due to stimulation and the baseline cortical potential is greater than an efficacy threshold. In response to this determination, monitoring device 40 may indicate that the electrical stimulation causing the cortical evoked potentials may be effective at treating fecal incontinence. In other words, monitoring device 40 may normalize the value of the characteristic (e.g., potential amplitude) to the baseline values and determine if the normalized value exceeds the efficacy threshold that indicates the electrical stimulation will be sufficient to reduce the symptoms of patient 12. The normalized value may be a percentage increase over the baseline value, an absolute value over the baseline value, or another suitable value.

In addition, or alternatively, system 10 may screen a plurality of different therapy parameter sets and the resulting different electrical stimulation to identify the most effective set of therapy parameter values. Stimulator 34 may be configured to, for each of the plurality of sets of therapy parameters to be tested, control the delivery of electrical stimulation at least partially defined by the respective set of therapy parameter values. Monitoring device 40 may then be configured to sense a respective cortical evoked potential from brain 16 of patient 12 that is indicative of responses of patient 12 to the delivery of electrical stimulation defined by each of the respective set of therapy parameter values. Monitoring device 40 may store the sensed cortical evoked potentials and determine respective values of one or more characteristics of the cortical evoked potentials.

For each of the respective cortical evoked potentials and therapy parameter value sets, monitoring device 40 may compare the respective values of the characteristic of the cortical evoked potential to the baseline value of the characteristic of the baseline cortical evoked potentials and determine the respective cortical evoked potential, and corresponding therapy parameter value set, with the value of the characteristic having the greatest difference relative to the baseline value of the characteristic of the baseline cortical evoked potentials. This determination may be based on the comparisons of the values of the characteristic of the cortical evoked potentials. Monitoring device 40 may then select, for electrical stimulation therapy, the set of therapy parameter values for which the determined respective cortical evoked potential was sensed. In other words, the therapy parameter value set causing the greatest increase, or decrease, in the cortical evoked potentials may be selected for electrical stimulation therapy.

Although monitoring device 40 is described as determining which therapy parameter sets may define effective electrical stimulation therapy, other devices or systems may perform the determination or analysis. For example, monitoring device 40 may transmit the stored values of the cortical evoked potentials to an external programmer 52 (of FIG. 2) such that programmer 52 can determine which therapy parameter sets to select for stimulation therapy. In other examples, monitoring device 40 may transmit the stored values of the cortical evoked potentials to a remote server via a network such that the remote server may determine therapy parameter value sets for stimulation therapy. In other examples, stimulator 34 and/or IMD 54 may perform such determination functions attributed to monitoring device 40 or programmer 52.

In some examples, the set of therapy parameter values selected for electrical stimulation to treat fecal incontinence may include pulses delivered at a certain frequency. For example, if stimulation comprises delivery of pulses, the pulse frequency may be selected from a range between 0.05

Hz and 50 Hz. In another example, the pulse frequency may be selected from a range between 0.1 Hz and 25 Hz. In still another example, the pulse frequency may be selected from a range between 0.5 Hz and 15 Hz. In one example, the pulse frequency may be selected from between approximately 1.0 and 3.0 Hz. These frequencies may elicit cortical evoked potentials and therapy related to fecal incontinence. However, these frequencies may also be effective in treating other disorders such as urinary incontinence or sexual dysfunction.

In some examples, certain values of the characteristics of the cortical evoked potentials and/or relative values may be indicative of effective therapy. For example, an amplitude of a sensed cortical evoked potential that is greater than or equal to 150% of the baseline potential amplitude may be indicative of effective electrical stimulation. In some examples, amplitudes of the sensed cortical evoked potential may greater than 120% of the baseline potential amplitude and still be indicative of effective electrical stimulation. Duration of elevated cortical evoked potentials amplitudes may also be indicative of effective electrical stimulation therapy. For example, a duration of the elevated cortical evoked potential amplitudes greater than 60 minutes may be indicative of effective therapy.

Screening for effective therapies may also include looking to maximize relief of symptoms while minimizing patient discomfort resulting from the electrical stimulation. In this manner, baseline cortical evoked potentials may be collected from various pain areas of brain 16. In some examples, electrical stimulation parameter values may be selected to maximize cortical evoked potential changes to the brain region associated with rectum 22 while minimizing the cortical evoked potential changes to the brain region associated with the undesirable pain.

Although testing electrical stimulation delivered to patient 12 may be used to screen the electrical stimulation for use as therapy, other examples may indicate whether or not pharmaceutical therapy will be effective to treat the condition. For example, stimulation of a nerve or tissue affected by a pharmaceutical may be indicative of whether or now the pharmaceutical will be effective.

In the example shown in FIG. 1, lead 36 is cylindrical. Electrodes 38 leads 36 may be ring electrodes, segmented electrodes, or partial ring electrodes. Segmented and partial ring electrodes each extend along an arc less than 360 degrees (e.g., 90-120 degrees) around the outer perimeter of lead 36. In some examples, lead 36 may have a complex electrode geometry. An example of a complex electrode array geometry may include an array of electrodes located at different axial positions along the length of a lead in addition to electrodes located at different angular positions about the periphery, e.g., circumference, of the lead 36. In examples, lead 36 may be, at least in part, paddle-shaped (i.e., a "paddle" lead). In some examples, one or more of electrodes 38 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12. An electrical field represents the areas of a patient anatomical region that will be covered by an electrical field during delivery of stimulation therapy to tissue within patient 12. The electrical field may define the volume of tissue that is affected when the electrodes 38 are activated. An activation field represents the neurons that will be activated by the electrical field in the neural tissue proximate to the activated electrodes.

Monitoring device 40 may be a wearable communication device, handheld computing device, computer workstation, or networked computing device. Monitoring device 40 may include a user interface that receives input from a user (e.g., patient 12, a patient caretaker or a clinician). The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Monitoring device 40 can additionally or alternatively include a peripheral pointing device, such as a mouse, via which a user may interact with the user interface. In some examples, a display of monitoring device 40 may include a touch screen display, and a user may interact with monitoring device 40 via the display. It should be noted that the user may also interact with monitoring device 40 and/or stimulator 34 remotely via a networked computing device (e.g., a networked server).

Monitoring device 40 and stimulator 34 may communicate via a wired connection or via wireless communication using any techniques known in the art. Examples of communication techniques may include, for example, low frequency or radiofrequency (RF) telemetry, but other techniques are also contemplated. In some examples, monitoring device 40 may include a programming head that may be placed proximate to the patient's body near the implant site in order to improve the quality or security of communication between monitoring device 40 and stimulation 34.

The example of FIG. 1 is directed to treating fecal incontinence via electrical stimulation directed to the second sacral nerve 32. However, fecal incontinence may be treated by stimulating one or more other nerves in addition or alternative to second sacral nerve 32. For example, stimulation may be directed to one or more of a pelvic floor nerve, a pelvic floor muscle, the anal sphincter, or other pelvic floor targets. Pelvic floor nerves include peripheral nerves such as sacral nerves, pudendal nerves and associated branches, and dorsal genital nerves.

Although the use of cortical evoked potentials to evaluate potential therapy for pelvic floor disorders is described herein, cortical evoked potentials may be used as a biomarker indicative of patient responsiveness to any type of therapy. In other words, the technique may include determining a relationship or correlation between an anatomical region of interest and an identified location of the cerebral cortex from which cortical potentials are evoked from any activity at the anatomical region. Once this relationship is known, a clinician or system may deliver stimulation to the anatomical region, or a nerve innervating the anatomical region, and look for cortical evoked potentials at the identified location. In other words, the cortical evoked potentials at the identified location may be a biomarker for effective stimulation. Sensing cortical evoked potentials at the identified location correlated with the target anatomical region may indicate that patient is responsive to the stimulation (e.g., the stimulation may be therapeutic). A lack of sensed cortical evoked potentials at the identified location may indicate that the patient may not respond, or be treated by, that particular stimulation. In some examples, this method may also be used to screen multiple therapies (e.g., electrical stimulation defined by different therapy parameter sets and/or different medications and/or dosages). This process may be used to evaluate treatments for motor dysfunction, organ dysfunction, pain, or any other condition. Monitoring cortical evoked potentials may allow a potential therapy to be evaluated without needing to monitor for any changes to the symptoms of the patient's condition, which may be difficult to obverse or occur over long time periods.

Once one or more therapy parameter value sets are selected for stimulation therapy, an implantable medical device (IMD) may be implanted within patient 12 for chronic, or long term, treatment of fecal incontinence. However, therapy may also include feedback to control the therapy over time. For example, FIG. 2 provides an example therapy system 50.

Figure 2:
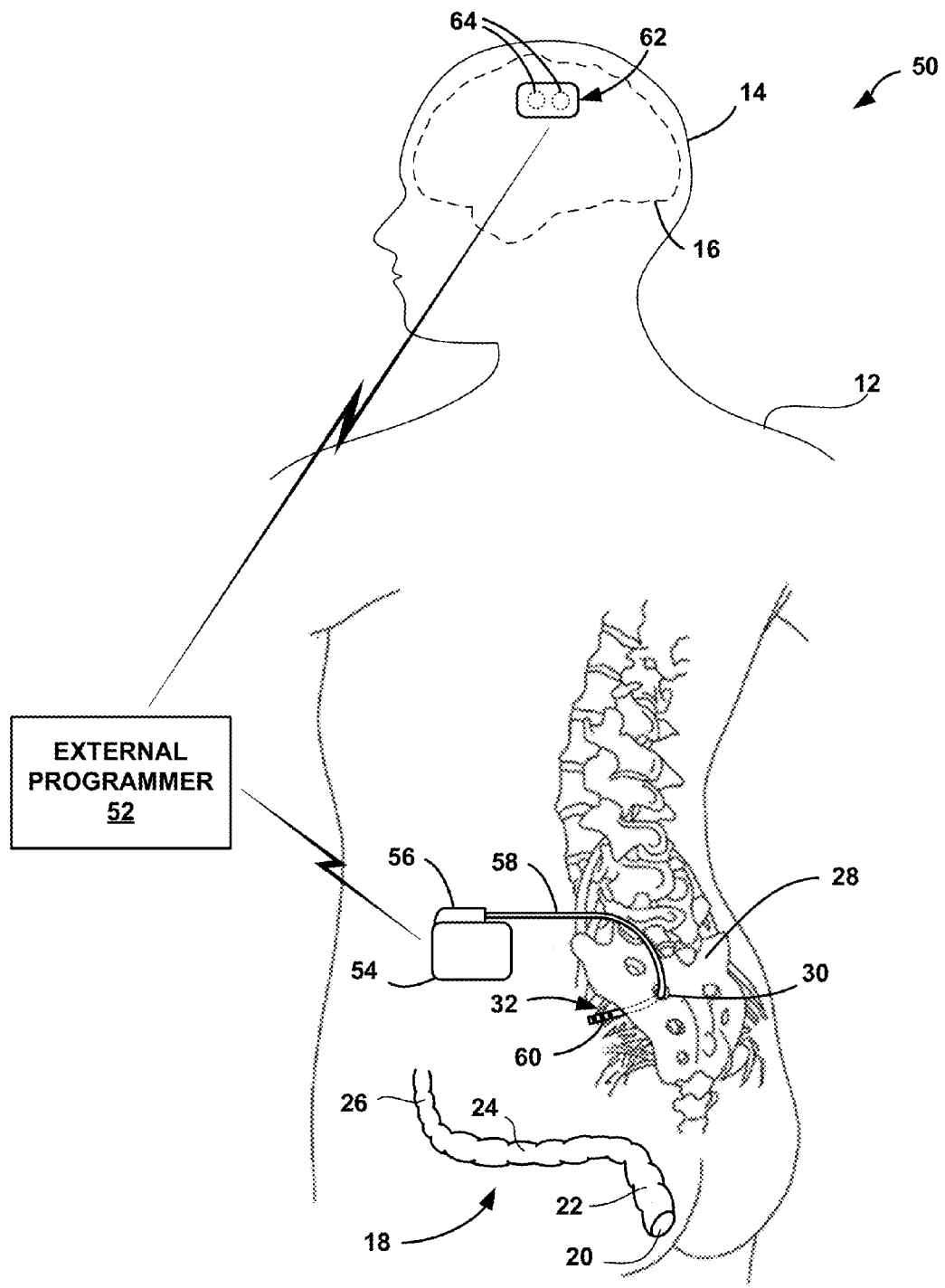
FIG. 2 is a conceptual diagram illustrating an example system configured to deliver electrical stimulation therapy and control therapy based on sensed cortical evoked potentials.

FIG. 2 is a conceptual diagram illustrating example system 50 that is configured to deliver electrical stimulation therapy and control therapy based on sensed cortical evoked potentials. System 50 may be similar to system 10 of FIG. 1, but system 50 may be configured for chronic use. As shown in FIG. 2, therapy system 10 includes an implantable medical device (IMD) 54, which is coupled to lead 58, sensor 62, and external programmer 52. IMD 54 generally operates as a therapy device that delivers electrical stimulation to, for example, the second sacral nerve 32 and/or other spinal nerves (e.g., the S3 nerve), a pelvic floor nerve, a pelvic floor muscle, the anal sphincter, or other pelvic floor targets. IMD 54 provides electrical stimulation therapy to patient 12 by generating and delivering a programmable electrical stimulation signal (e.g., in the form of electrical pulses or a waveform) to a target therapy site by lead 58 and, more particularly, via electrodes 60 disposed proximate to a distal end of lead 58.

IMD 54 may be surgically implanted in patient 12 at any suitable location within patient 12, such as near the pelvis. The implantation site may be a subcutaneous location in the side of the lower abdomen or the side of the lower back or upper buttocks. IMD 54 has a biocompatible housing, which may be formed from titanium, stainless steel, a liquid crystal polymer, or the like. The proximal ends of lead 58 may be both electrically and mechanically coupled to IMD 54 via connector block 56 either directly or indirectly, e.g., via a respective lead extension. Electrical conductors disposed within the lead body of lead 58 electrically connect stimulation electrodes, such as electrodes 60, to a therapy delivery module (e.g., a stimulation generator) within IMD 54.

External programmer 52 may be configured to control IMD 54 to deliver electrical stimulation according to the therapy parameter values selected previously based on sensed cortical evoked potentials. External programmer 52 may transmit the therapy parameter value sets for IMD 54 and/or communicate with IMD 54 for other reasons. External programmer 52 may be configured to wirelessly communicate with IMD 54. Programmer 52 may also receive data collected by IMD 54.

Electrical stimulation therapy may also be adjusted over time based on one or more feedback mechanisms. For example, sensor 62 may continue to monitor cortical evoked potentials during stimulation therapy. Sensor 62 may include two or more electrodes 64 (surface electrodes or implanted electrodes), any other components such as a processor, memory, power source, and telemetry module required to sense cortical evoked potentials, store the sensed cortical evoked potentials, and transmit the cortical evoked potentials to external programmer 52, IMD 54, or another device. A housing of sensor 62 may be external or implanted. Sensor 62, and electrodes 64, may be placed at any location with respect to head 14 or brain 16 sufficient to sense cortical evoked potentials as described herein. In response to receiving sensed cortical evoked potentials from sensor 62, external programmer 52 may compare one or more characteristics of the sensed cortical evoked potentials to baseline characteristic values and/or historical characteristic values of previously sensed cortical evoked potentials. Programmer 52 may adjust one or more therapy parameter values or sets of therapy parameter values to improve the efficacy of stimulation therapy. External programmer 52 may then transmit the adjusted therapy parameters to IMD 54.

Although sensor 62 is described as communicating with external programmer 52, sensor 62 may additionally or alternatively communicate with IMD 54. For example sensor 62 may directly send indications of the cortical evoked potentials to IMD 54, which may adjust stimulation therapy in response to the sensed cortical evoked potentials. In some examples, sensor 62 may be directly, rather than wirelessly, coupled to IMD 54 (e.g., via a lead tunneled through the patient's neck.)

System 50 may also include an external programmer 52, as shown in FIG. 2. In some examples, programmer 52 may be a wearable communication device integrated into a key fob or a wrist watch, handheld computing device, computer workstation, or networked computing device. Programmer 52 may include a user interface that receives input from a user (e.g., patient 12, a patient caretaker or a clinician). The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 52 can additionally or alternatively include a peripheral pointing device, such as a mouse, via which a user may interact with the user interface. In some examples, a display of programmer 52 may include a touch screen display, and a user may interact with programmer 52 via the display. It should be noted that the user may also interact with programmer 52 and/or IMD 54 remotely via a networked computing device.

IMD 54, sensor 62, and/or programmer 52 may communicate via wireless communication using any techniques known in the art. Examples of communication techniques may include, for example, low frequency or radiofrequency (RF) telemetry, but other techniques are also contemplated. In some examples, programmer 52 may include a programming head that may be placed proximate to the patient's body near the IMD 54 implant site in order to improve the quality or security of communication between IMD 54 and programmer 52.

Figure 3:
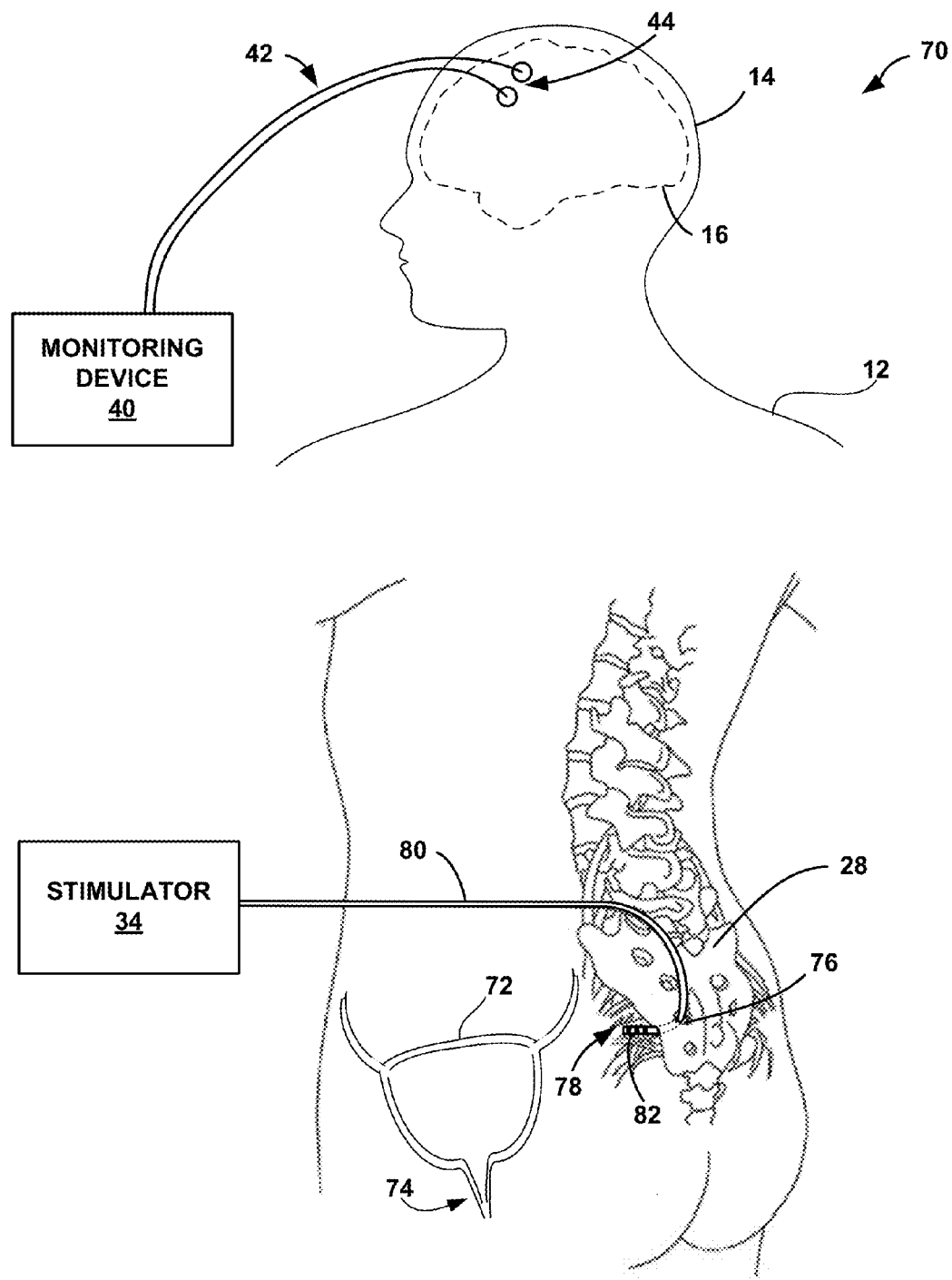
FIG. 3 is a conceptual diagram illustrating an example system configured to control delivery of electrical stimulation and sense cortical evoked potentials to screen for effective therapy to treat a bladder related condition of a patient.

FIG. 3 is a conceptual diagram illustrating example system 70 configured to control delivery of electrical stimulation and sense cortical evoked potentials to screen for effective therapy to treat a bladder related condition of patient 12. System 70 may be substantially similar to system 10 of FIG. 1. However, stimulator 34 and monitoring device 40 may be configured to deliver electrical stimulation configured to treat to urinary incontinence. Lead 80 may be substantially similar to lead 36 of FIG. 1 and electrodes 82 may be substantially similar to electrodes 38 of FIG. 1. However, lead 80 may be implanted such that the distal end of lead 80 is directed through sacral foramen 76 such that electrodes 82 are placed adjacent to third sacral nerve 78. Third sacral nerve 78 may innervate anatomical regions associated with urinary incontinence such as the muscular wall of bladder 72 and urinary sphincter 74. Additional or alternative nerves may also be targeted by one or more of electrodes 82. Electrodes 44 may be placed at any location with respect to head 14 and brain 16 sufficient to sense the cortical evoked potentials described herein.

As described above with respect to FIG. 1, system 70 may induce a sensation of bladder 72 and/or urinary sphincter 74. Monitoring device 40 may sense the resulting cortical evoked potentials to establish one or more baseline characteristic values of the potentials. Inducing the sensation may include waiting for bladder 72 to be full, inserting a catheter or balloon in the urethra, or providing electrical stimulation to bladder 72 or urinary sphincter 74. Stimulator 34 may deliver electrical stimulation to third sacral nerve 78 via one or more electrodes 82 of lead 80, and monitoring device 40 may sense cortical evoked potentials resulting from the stimulation. Based on the differences between the baseline potentials and the sensed cortical evoked potentials, monitoring device 40 may determine whether patient 12 will be responsive to the electrical stimulation therapy or other therapy, or, in some examples, determine one or more efficacious therapy parameter value sets or other therapies to treat urinary incontinence. Although not illustrated in a figure, an implantable system similar to system 50 described in FIG. 2 may be configured for chronic therapy directed to treating urinary incontinence based on the therapies identified through the processes of FIG. 3.

Figure 4:
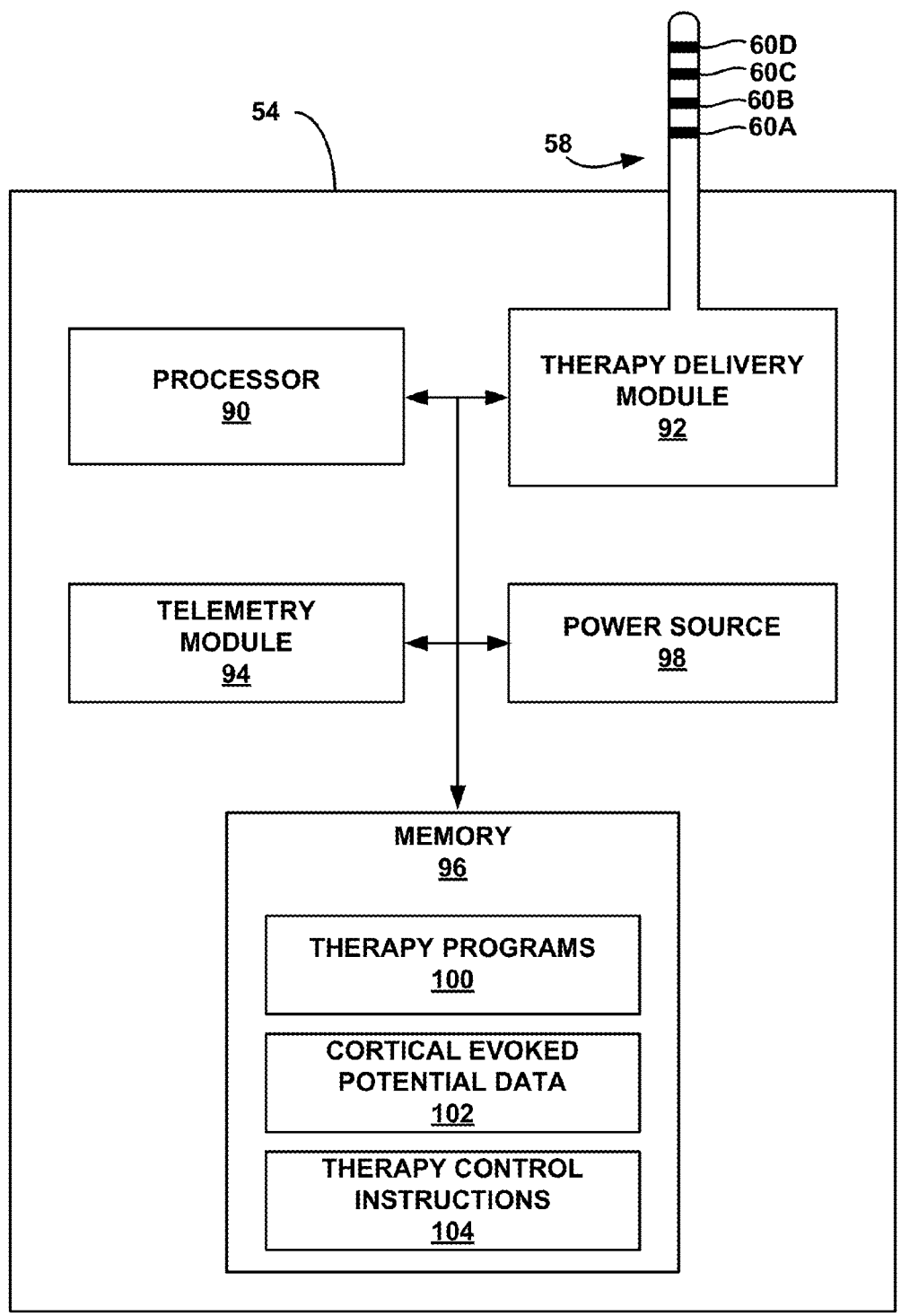
FIG. 4 is a block diagram illustrating an example configuration of the implantable medical device (IMD) of the system shown in FIG. 2.

FIG. 4 is a block diagram illustrating an example configuration of IMD 54 of system 50 shown in FIG. 2. Although FIG. 4 is directed to an IMD, the components and features of IMD 54 may be similar to the components and features of stimulator 34 described in FIGS. 1 and 3. In the example of FIG. 4, IMD 54 includes one or more processors 90, therapy delivery module 92, memory 96, telemetry module 94, and power source 98. Memory 96 stores therapy programs 100, cortical evoked potential data 102, and therapy control instructions 104.

Generally, therapy delivery module 92 is configured to generate and deliver therapy under the control of processor 90. In some examples, processor 90 controls therapy delivery module 92 by accessing memory 96 to selectively accessing and loading an appropriate therapy program 100 (e.g., a set of therapy parameter values) according to therapy control instructions 104. For example, in operation, processor 90 may access memory 96 to load one of stimulation therapy programs 100 to therapy delivery module 92 based on the evaluation of electrical stimulation using sensed cortical evoked potentials.

By way of example, processor 90 may access memory 96 to load one of therapy programs 100 to therapy delivery module 92 for delivering the stimulation therapy to patient 12. A clinician or patient 12 may select a particular one of stimulation therapy programs 100 from a list using a programming device, such as programmer 52. The selected program may be identified as a likely effective program based on the sensed cortical evoked potentials. Processor 90 may receive the selection via telemetry module 94. Therapy delivery module 92 delivers the first stimulation therapy to patient 12 according to the selected program for an extended period of time, such as hours, days, weeks, or until patient 12 or a clinician manually stops or changes the program. In other examples, processor 90 may automatically select one or more therapy programs 100 based on cortical evoked potential data 102.

Therapy delivery module 92 delivers therapy, i.e., electrical stimulation, according to therapy parameters, such as voltage or current amplitude, pulse rate (frequency), and pulse width specified by therapy programs, such as one of therapy programs 100. Additional therapy parameters may include a burst frequency or duration, electrode configuration (e.g., polarity such as bipolar, multipolar, unipolar), electrode combination, waveshape (for continuous waveforms), a cycling on/off parameter indicating whether stimulation is always on or whether it is cycled on and off, and a duty cycle. In some examples, therapy delivery module 92 delivers therapy in the form of electrical pulses. In other examples, therapy delivery module 92 delivers electrical stimulation in the form of continuous waveforms.

In some examples, the stimulation parameters for the stimulation programs 100 may be selected to relax rectum 22 (FIG. 1) or close or maintain an anal sphincter closure or tone. An example range of stimulation parameter values for the first stimulation therapy that are likely to be effective in treating incontinence, e.g., when applied to the sacral or pudendal nerves, are as follows:

1. Frequency: between approximately 0.05 Hz and approximately 50 Hz, such as between approximately 0.1 Hz and approximately 25 Hz, or between approximately 0.5 Hz and approximately 10 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds (μs) and approximately 5000 μs, such as between approximately 100 μs and approximately 1000 μs, or between approximately 180 μs and approximately 450 μs.

As described above, therapy programs 100 may include one or more therapy programs that have been identified as potentially effective as treating the patient's condition, e.g., fecal incontinence, by evaluating corresponding cortical evoked potentials. Alternatively, therapy programs 100 may store a plurality of therapy programs, and processor 90 may select one or more of the stored therapy programs based on the sensed cortical evoked potentials (e.g., therapy programs having one or more therapy parameter values corresponding to a characteristic value of the cortical evoked potentials). Therapy programs 100 may each include a unique set of therapy parameter values that define electrical stimulation therapy. In some examples, the therapy programs 100 may be ranked according to potential effectiveness or otherwise organized in order of use for delivery of therapy.

Cortical evoked potential data 102 may include any values of characteristics of cortical evoked potential data collected for respective therapy programs. Cortical evoked potential data 102 may be loaded from monitoring device 40 and/or generated from the cortical evoked potentials received from sensor 62. Therapy control instructions 104 may include instructions for IMD 54 regarding when to choose which one of therapy programs 100, how and when to use feedback data, and any other instructions related to the continued delivery of electrical stimulation therapy.

In the example of FIG. 4, therapy delivery module 92 drives a single lead 58. Specifically, therapy delivery module 92 delivers electrical stimulation to tissue of patient 12 via selected electrodes 60A-60D (collectively referred to as "electrodes 60") carried by lead 58. A proximal end of lead 58 extends from the housing of IMD 54 and a distal end of lead 58 extends to target therapy sites within the pelvic floor, such as the second and/or third sacral nerve, a pudendal nerve, a hypogastric nerve, an anal sphincter, or any combination thereof. In other examples, therapy delivery module 92 may deliver electrical stimulation with electrodes on more than one lead and each of the leads may carry one or more electrodes. The leads may be configured as an axial leads with ring electrodes and/or paddle leads with electrode pads arranged in a two-dimensional array. Alternatively, the electrodes may be configured in a complex array geometry as discussed above. The electrodes may operate in a bipolar or multi-polar configuration with other electrodes, or may operate in a unipolar configuration referenced to an electrode carried by the device housing or "can" of IMD 54.

Processor 90 may control delivery of therapy according to previously selected therapy parameter values and/or sensed cortical evoked potentials sensed during therapy. In some examples, the sensed cortical evoked potentials may be received wirelessly from sensor 62 (FIG. 2) or directly via a wired connection to electrodes 64. IMD 54 may also include one or more sensors as feedback to control stimulation therapy. The output from these one or more sensors may be, in some examples, combined with the sensed cortical evoked potentials to determine the effectiveness of therapy and allow processor 90 to adjust one or more therapy parameter values as needed.

The one or more sensors may include one or more of a pressure sensor for detecting changes in rectal pressure, electrodes for sensing pudendal or sacral afferent nerve signals, or electrodes for sensing external anal sphincter signals, or any combination thereof. Alternatively, a sensor may be a motion sensor, such as a two-axis accelerometer, three-axis accelerometer, one or more gyroscopes, pressure transducers, piezoelectric crystals, or other sensors that generate a signal that changes as patient activity level or posture state changes. Processor 90 may, for example, detect a patient condition indicative of a high probability of an incontinence event (e.g., rectal contraction or abnormal muscle activity) or other trigger events based on signals received from the sensor in addition to or instead of any other feedback.

Telemetry module 94 includes any suitable hardware, firmware, software or any combination thereof for communicating with another device, such as programmer 52 (FIG. 2). Under the control of processor 90, telemetry module 94 may receive downlink telemetry, e.g., patient input, from and send uplink telemetry, e.g., an alert, to programmer 24 with the aid of an antenna, which may be internal and/or external. Processor 90 may provide the data to be uplinked to programmer 24 and the control signals for the telemetry circuit within telemetry module 94, and receive data from telemetry module 94.

Generally, processor 90 controls telemetry module 94 to exchange information with one or more other devices, such as medical device programmer 52. Processor 90 may transmit operational information and receive stimulation programs or stimulation parameter adjustments via telemetry module 94. Also, in some examples, IMD 54 may communicate with other implanted devices, such as stimulators, control devices, or sensors, via telemetry module 94.

The processors described in this disclosure, such as processor 90 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof.

Memory 96 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 96 may store program instructions that, when executed by processor 90, cause IMD 54 to perform the functions ascribed to IMD 54 herein. Memory 96 may be described as a storage device in some examples.

Power source 98 delivers operating power to the components of IMD 54. Power source 98 may include a battery and a power generation circuit to produce the operating power. In some examples, the battery may be rechargeable to allow extended operation. Recharging may be accomplished through proximal inductive interaction between an external charger and an inductive charging coil within IMD 54. In other examples, an external inductive power supply may transcutaneously power IMD 54 whenever stimulation therapy is to occur. In other examples, the battery of power source 98 may include a prime cell device.

Figure 5:
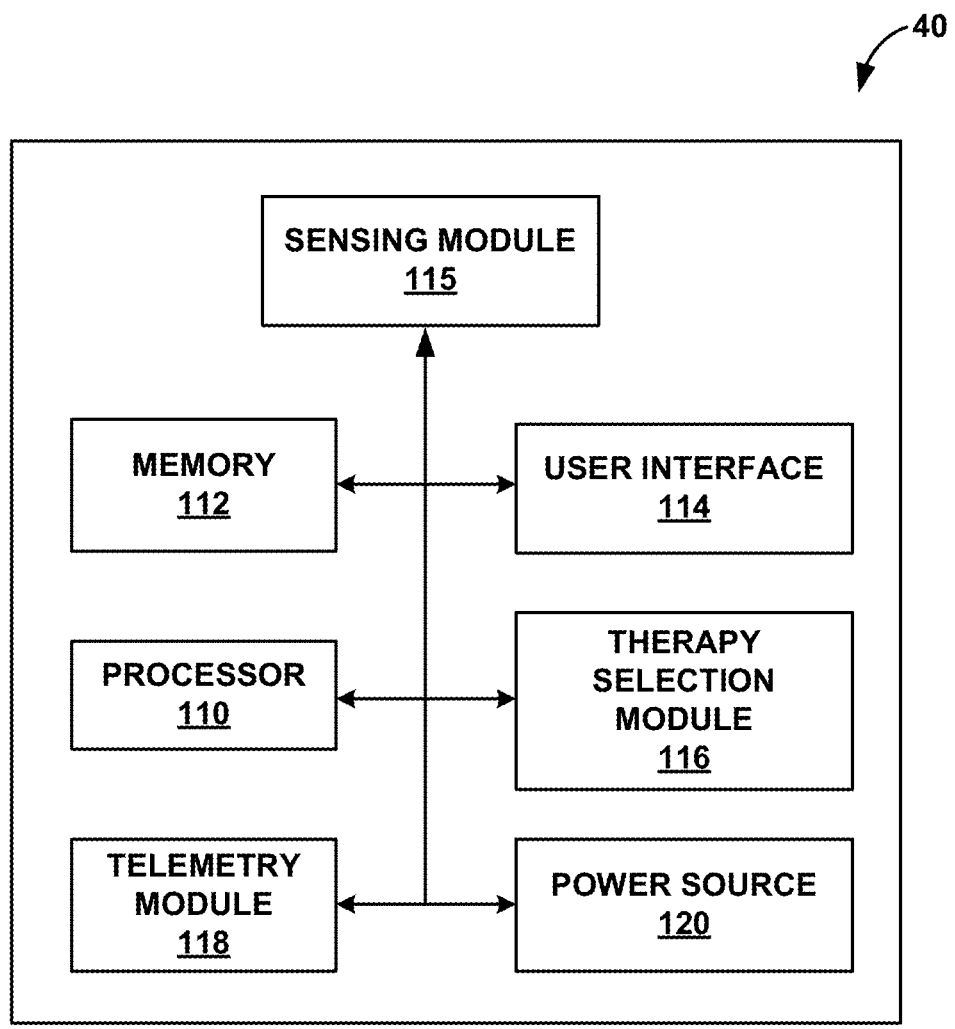
FIG. 5 is a block diagram illustrating an example configuration of a monitoring device of the system shown in FIGS. 1 and 3.

FIG. 5 is a block diagram illustrating an example configuration of monitoring device 40 of systems 10 and 70 shown in FIGS. 1 and 3, respectively. While monitoring device 40 may generally be described as a hand-held computing device, the device may be a notebook computer, a cell phone, or a workstation, in other examples. As illustrated in FIG. 5, external monitoring device 40 may include one or more processors 110, memory 112, user interface 114, sensing module 115, therapy selection module 116, telemetry module 118, and power source 120. Memory 112 may store monitoring instructions that, when executed by processor 110, cause processor 110 and external monitoring device 40 to provide the functionality ascribed to external monitoring device 40 throughout this disclosure. Memory 112 may also store cortical evoked potentials and/or calculated values of characteristics of the cortical evoked potentials.

Memory 112 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Memory 112 may be described as a storage device containing instructions that cause a processor to perform various functions. Processor 110 can take the form one or more microprocessors, DSPs, ASICs, FPGAs, programmable logic circuitry, or the like, and the functions attributed to processor 110 herein may be embodied as hardware, firmware, software or any combination thereof.

User interface 114 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 110 may present and receive information relating to sensed cortical evoked potentials and/or stimulation delivered to patient 12 via user interface 114. For example, processor 110 may receive patient input via user interface 114. The input may be, for example, in the form of pressing a button on a keypad or selecting an icon from a touch screen.

Telemetry module 118 supports wireless communication between monitoring device 40, for example, under the control of processor 110. Telemetry module 118 may also be configured to communicate with another computing device via wireless communication techniques, or direct communication through a wired connection. In some examples, telemetry module 118 may include an antenna, which may take on a variety of forms, such as an internal or external antenna. Examples of local wireless communication techniques that may be employed to facilitate communication between monitoring device 40 and another computing device include RF communication according to the 802.11 or Bluetooth specification sets, infrared communication, e.g., according to the IrDA standard, or other standard or proprietary telemetry protocols. In this manner, other external devices may be capable of communicating with monitoring device 40 without needing to establish a secure wireless connection.

Sensing module 115 may be configured to couple to one or more electrodes 44 via respective leads 42. Sensing module 115 may be configured to sense cortical evoked potentials generated from patient 12. Sensing module 115 may include components that allow the desired electrodes to provide a sensing vector for cortical evoked potentials of a desired brain region. Sensing module 115 may also include components configured to calculate values for one or more characteristics representing the sensed cortical evoked potentials. Therapy selection module 116 may include instructions for comparing sensed cortical evoked potentials to baseline potentials and selecting therapies likely to be effective in treating the condition of patient 12.

Power source 120 delivers operating power to the components of monitoring device 40. Power source 120 may include a battery and a power generation circuit to produce the operating power. In some examples, the battery may be rechargeable to allow extended operation. Recharging may be accomplished by electrically coupling power source 120 to a cradle or plug that is connected to an alternating current (AC) outlet. In addition or alternatively, recharging may be accomplished through proximal inductive interaction between an external charger and an inductive charging coil within monitoring device 40. In other examples, traditional batteries (e.g., nickel cadmium or lithium ion batteries) may be used. In addition, monitoring device 40 may be directly coupled to an alternating current outlet to power monitoring device 40. Power source 120 may include circuitry to monitor power remaining within a battery. In this manner, user interface 114 may provide a current battery level indicator or low battery level indicator when the battery needs to be replaced or recharged. In some cases, power source 120 may be capable of estimating the remaining time of operation using the current battery.

The example of monitoring device 40 may be directed to sensing electroencephalograms from patient 12. However, monitoring device 40 may be configured differently depending upon the type of signals being monitored. For example, monitoring device 40 may include an MRI system if the cortical evoked potentials are to be sensed using functional MRI techniques. In other examples, monitoring device 40 may be configured to detect cortical evoked potentials using positron emission tomography (PET), or direct recording by electrodes. In this manner, monitoring device 40 may be a hand-held device or room-sized system.

Figure 6:
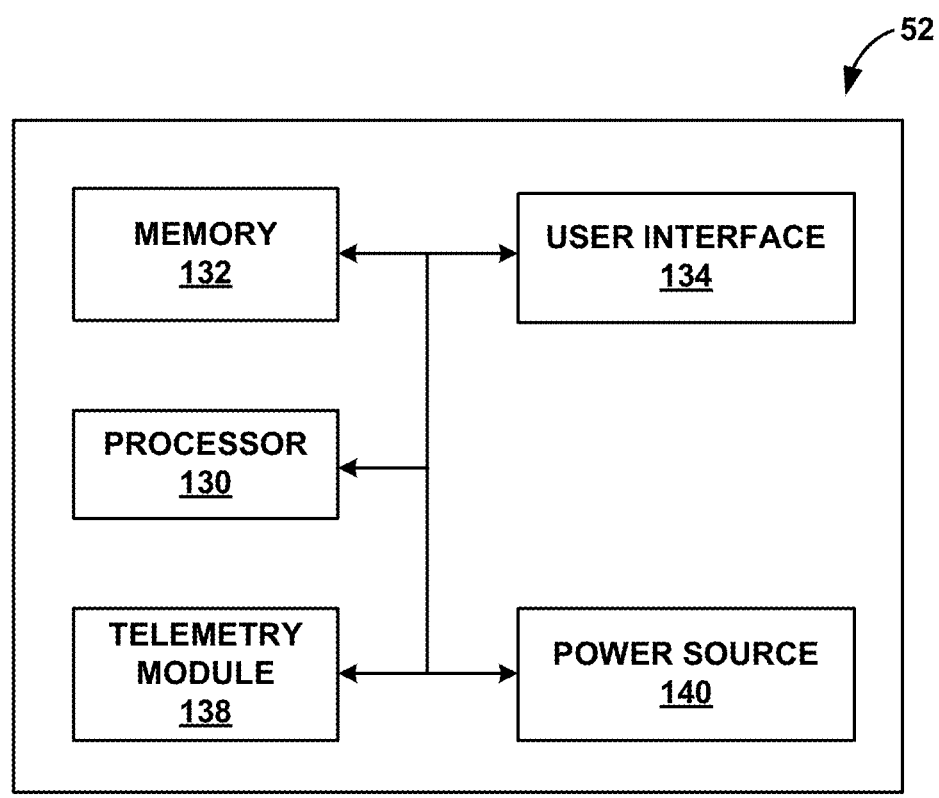
FIG. 6 is a block diagram illustrating an example configuration of the external programmer of the system shown in FIG. 2.

FIG. 6 is a block diagram illustrating an example configuration of external programmer 52 of system 50 shown in FIG. 2. While programmer 52 may generally be described as a hand-held computing device, the programmer may be a notebook computer, a cell phone, or a workstation, for example. As illustrated in FIG. 6, external programmer 52 may include a processor 130, memory 132, user interface 134, telemetry module 138, and power source 140. Memory 132 may store program instructions that, when executed by processor 130, cause processor 130 and external programmer 52 to provide the functionality ascribed to external programmer 52 throughout this disclosure.

In some examples, memory 132 may further include program information, i.e., therapy programs each having a set of therapy parameter values that define stimulation therapy. In other examples, memory 132 may also store two or more therapy programs to be evaluated by patient 12 for efficacy. The therapy programs for evaluation may have been selected based on the cortical evoked potentials sensed and compared to baseline cortical evoked potentials. In some examples, the therapy programs stored in memory 132 may be downloaded into memory 96 of IMD 54. Memory 132 (e.g., a storage device) may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 130 can take the form one or more microprocessors, DSPs, ASICs, FPGAs, programmable logic circuitry, or the like, and the functions attributed to processor 130 herein may be embodied as hardware, firmware, software or any combination thereof.

User interface 134 may include a button or keypad, lights, a speaker for voice commands, a display, such as a LCD, LED, or CRT. In some examples the display may be a touch screen. As discussed in this disclosure, processor 130 may present and receive information relating to stimulation therapy via user interface 134. For example, processor 130 may receive patient input via user interface 134. The input may be, for example, in the form of pressing a button on a keypad or selecting an icon from a touch screen.

Telemetry module 138 supports wireless communication between IMD 54 and external programmer 52 under the control of processor 130. In addition, telemetry module 138 may support communication with sensor 62 to receive sensed cortical evoked potentials for feedback during therapy or therapy evaluation. In some examples, programmer 52 may be configured to control sensor 62, such as request the sensing of cortical evoked potentials. Telemetry module 138 may also be configured to communicate with another computing device via wireless communication techniques, or direct communication through a wired connection. Telemetry module 138 may be substantially similar to telemetry module 94 described above, providing wireless communication via an RF or proximal inductive medium. In some examples, telemetry module 138 may include an antenna, which may take on a variety of forms, such as an internal or external antenna. An external antenna that is coupled to programmer 52 may correspond to a programming head that may be placed over IMD 54.

Examples of local wireless communication techniques that may be employed to facilitate communication between programmer 52 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 52 without needing to establish a secure wireless connection.

Power source 140 delivers operating power to the components of programmer 52. Power source 140 may include a battery and a power generation circuit to produce the operating power. In some examples, the battery may be rechargeable to allow extended operation. Recharging may be accomplished by electrically coupling power source 140 to a cradle or plug that is connected to an alternating current (AC) outlet. In addition or alternatively, recharging may be accomplished through proximal inductive interaction between an external charger and an inductive charging coil within programmer 52. In other examples, traditional batteries (e.g., nickel cadmium or lithium ion batteries) may be used. In addition, programmer 52 may be directly coupled to an alternating current outlet to power programmer 52. Power source 140 may include circuitry to monitor power remaining within a battery. In this manner, user interface 134 may provide a current battery level indicator or low battery level indicator when the battery needs to be replaced or recharged. In some cases, power source 140 may be capable of estimating the remaining time of operation using the current battery.

Figure 7:
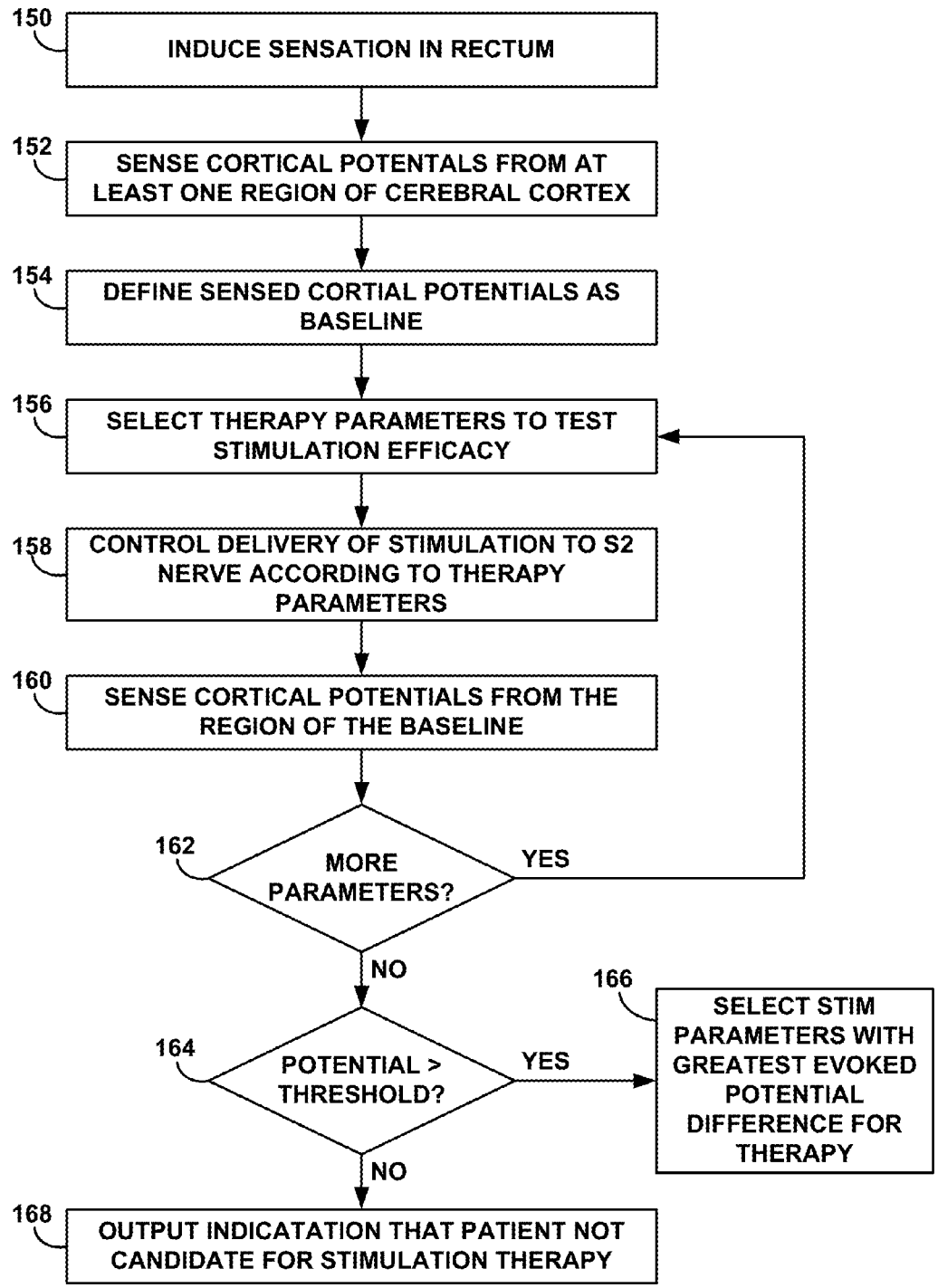
FIG. 7 is a flow diagram illustrating an example technique for screening multiple sets of therapy parameters to identify efficacious electrical stimulation therapy from sensed cortical evoked potentials.

FIG. 7 is a flow diagram illustrating an example technique for screening multiple sets of therapy parameter values to identify efficacious electrical stimulation therapy from sensed cortical evoked potentials. The process of FIG. 7 will be described with respect to stimulator 34 and monitoring device 40 in relation to fecal incontinence of FIG. 1. However, the process of FIG. 7 may be performed by other devices such as IMD 54, programmer 52, and sensor 62 or for other conditions such as urinary incontinence, as described with respect to FIG. 3.

In the technique shown in FIG. 7, baseline cortical evoked potentials are obtained. A clinician, patient, or stimulator 34 may induce a sensation in rectum 22 (150). This sensation may be induced by the presence of fecal matter, an objected inserted into the rectum, or even electrical stimulation directed at the rectum as a target anatomical region. Monitoring device 40 senses cortical evoked potentials resulting from the induced sensation from at least one region of the cerebral cortex of patient 12 (152). In some examples, monitoring device 40 continually monitors cortical potentials prior to the sensation inducement (150), while in other examples, monitoring device 40 initiates the monitoring of cortical potentials in response to receiving some input or otherwise detecting the inducement of the sensation in rectum 22 (150).

Processor 110 of monitoring device 40 receives the sensed cortical evoked potentials and defines the sensed cortical evoked potentials as the baseline for rectum 22 (154). Defining the sensed cortical evoked potentials as the baseline may include determining values of one or more characteristics (also referred to herein as "baseline characteristics") representing the sensed cortical evoked potentials. For example, the characteristics may include an amplitude, duration of elevated potentials, and latency between stimulation and elevated potentials. Processor 110 can, for example, store the baseline cortical evoked potentials, the baseline characteristics, or both, in memory 112 of monitoring device 40 or a memory of another device.

In the technique shown in FIG. 7, stimulator 34 may then select a set of therapy parameter values to test stimulation efficacy (156) and control delivery of stimulation to the second sacral nerve 32 according to the selected set of therapy parameter values (158). In some examples, the stimulation delivered to sacral nerve 32 may be therapeutic or nontherapeutic. In other words, the delivered stimulation may be defined by therapy parameter values selected to induce a therapeutic result in patient 12. Alternatively, the delivered stimulation may be a nontherapeutic test stimulation defined by therapy parameter values selected only to determine whether or not patient 12 would be responsive to eventual therapeutic stimulation. However, the nontherapeutic stimulation may still elicit cortical evoked potentials that verify a correlation or relationship between the neural conduction pathway between the target stimulation site and the brain region. For example, therapeutic stimulation may exceed a perception threshold, motor threshold, and/or outcome threshold whereas the nontherapeutic stimulation may not exceed one of or all of these physiological thresholds. In response to delivery of the therapy, processor 110 may control monitoring device 40 to sense cortical evoked potentials (evoked in response to the delivery of therapy) from the brain region from which the baseline potentials were determine and receive the sensed cortical evoked potentials (160). Processor 110 may also determine values of one or more characteristics representing the respective sensed cortical evoked potentials.

If there are more therapy parameters or sets of therapy parameters to evaluate ("YES" branch of block 162), stimulator 34 may select new therapy parameters to test (156). If there are no more therapy parameters to evaluate ("NO" branch of block 162), processor 110 of monitoring device 40 may compare the difference between one or more of the characteristic values of the sensed cortical evoked potentials and the baseline characteristics to an efficacy threshold (164). If none of the characteristic values of the sensed cortical evoked potentials exhibit a difference relative to the one or more baseline characteristics that is greater than the efficacy threshold ("NO" branch of block 164), then processor 110 may output an indication that patient 12 is not a candidate for stimulation therapy to treat fecal incontinence (168). The indication can be provided, for example, as a visible, audible, or somatosensory indication presented via user interface 114 (FIG. 5).

If at least one of the characteristic values of the sensed cortical evoked potentials exhibits a difference relative to the one or more baseline characteristics and that difference is greater than the efficacy threshold ("YES" branch of block 164), then processor 110 may select the therapy parameter value set with the greatest difference between the respective characteristic values of the sensed cortical evoked potentials and the baseline characteristic value (166). In some examples, processor 110 may select the top few therapy parameter sets so that patient 12 can evaluate the efficacy of each therapy parameter set likely to provide efficacious therapy. The greatest difference between sensed cortical evoked potentials may be between amplitudes of the baseline potentials and the sensed cortical evoked potentials, between the durations of elevated sensed cortical evoked potentials (elevated relative to the baseline), and/or latency between the beginning of therapy and elevated amplitudes of the sensed cortical evoked potentials.

Figure 8:
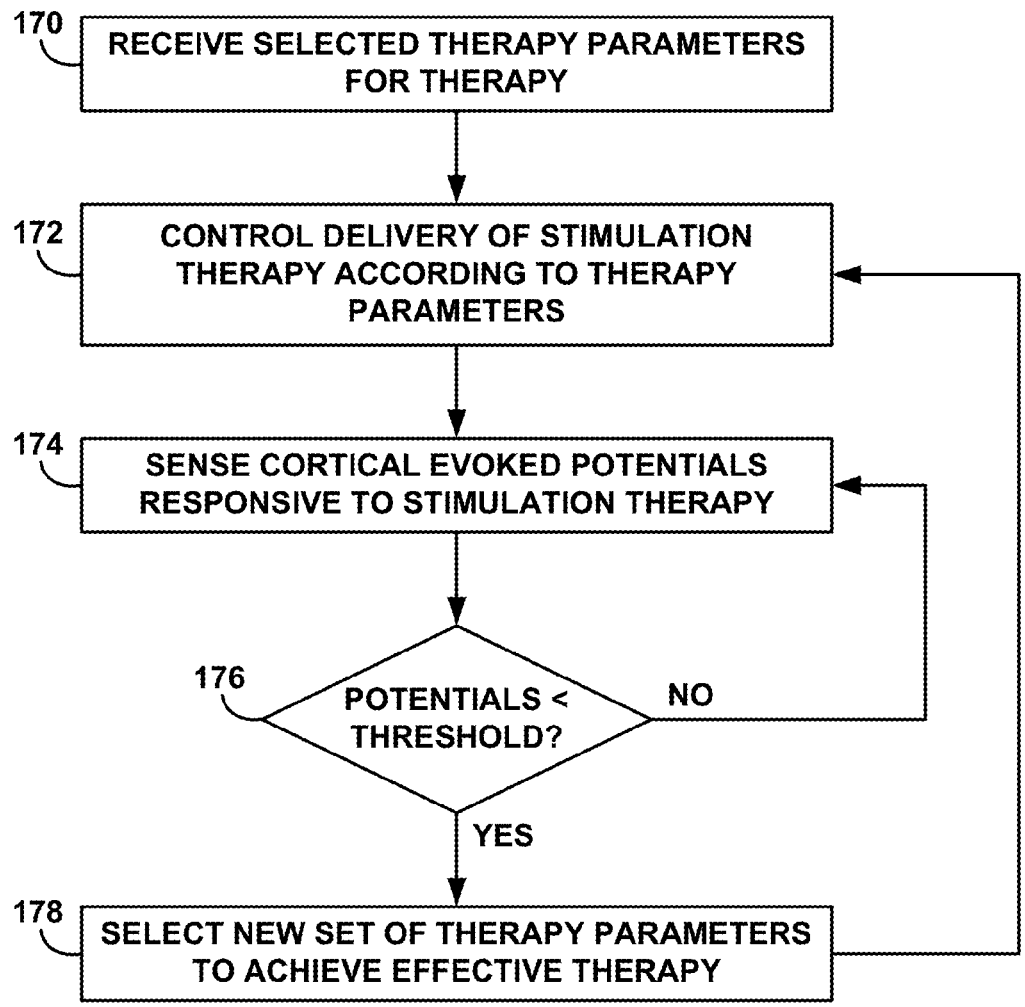
FIG. 8 is a flow diagram illustrating an example technique for controlling electrical stimulation therapy based on sensed cortical evoked potentials.

FIG. 8 is a flow diagram illustrating an example technique for controlling electrical stimulation therapy based on sensed cortical evoked potentials. FIG. 8 is described with respect to processor 90 of IMD 54 and sensor 64. However, the process for using sensed cortical evoked potentials as feedback during therapy may be utilized or at least partially performed by any of stimulator 34, monitoring device 40, or programmer 52.

Processor 90 of IMD 54 receives a selected set of therapy parameter values for delivery of electrical stimulation therapy (170). The selected set of therapy parameter values may be selected based on a comparison (e.g., by monitoring device 40) between sensed cortical evoked potentials and baseline potentials, e.g., using the technique described with respect to FIG. 7. Processor 90 may then control delivery of electrical stimulation therapy by therapy delivery module 92 according to the selected set of therapy parameter values (172). Sensor 62 senses cortical evoked potentials evoked by the electrical stimulation therapy (174). Sensor 62 may transmit the sensed cortical evoked potentials to processor 90, and processor 90 may determine values of the characteristics of the sensed cortical evoked potentials.

If processor 90 determines that any of the determined characteristic values are greater than the efficacy threshold ("NO" branch of block 176), then processor 90 may continue to control sensor 62 to sense cortical evoked potentials (174). If processor 90 determines that any of the determine characteristic values are less than the efficacy threshold ("YES" branch of block 176), then processor 90 may select a new set of therapy parameter values to attempt to achieve increased efficacy (178). Processor 90 may select a new set of therapy parameter values from memory 96 or initialize another evaluation or screening of possible therapy parameters. Processor 90 may then continue to control delivery of stimulation therapy according to the new set of therapy parameter values.

The technique shown in FIG. 8 may be useful for automatically or, with the aid of some user input, updating one or more therapy parameter values to help account for adaptation of patient 12 to a set of therapy parameter values, movement of lead 58 (FIG. 4), or another reason for a reduction in efficacy of a set of therapy parameter values. In some cases, e.g., due to adaptation or lead migration, the same set of therapy parameter values may become less effective over time. The technique shown in FIG. 8 may be useful for IMD 54, programmer 52, or another device to determine when the efficacy of a particular set of therapy parameter values has decreased, and, in response, periodically adjusting the therapy parameter values to help improve the efficacy of therapy delivery.

Figure 9:
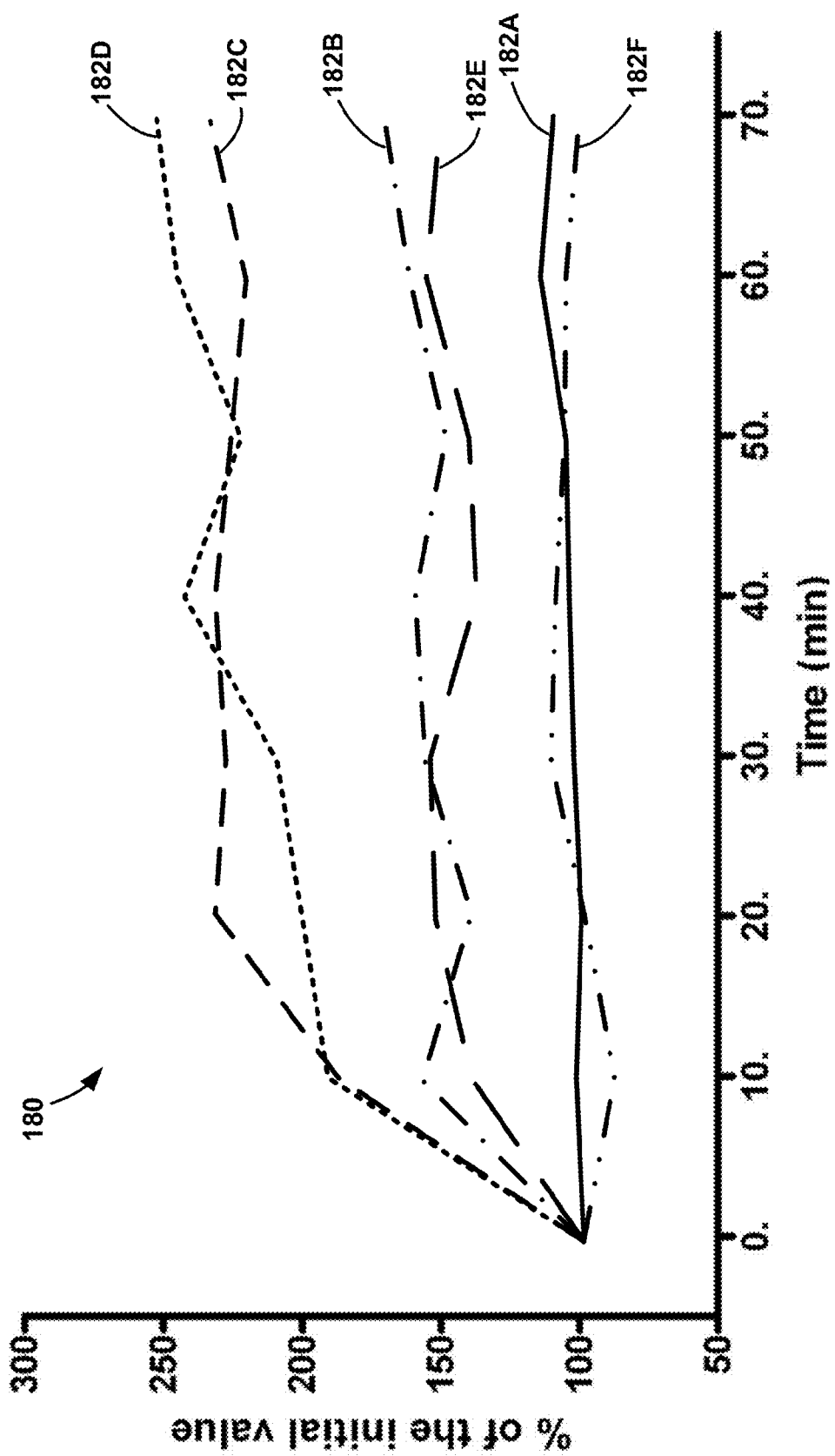
FIG. 9 is a graph illustrating example normalized amplitude increases of cortical evoked potentials sensed in response to electrical stimulation therapy defined by different pulse frequencies.

FIG. 9 is a graph illustrating example normalized amplitude increases of cortical evoked potentials sensed in response to electrical stimulation therapy defined by different pulse frequencies. The data shown in FIG. 9 was obtained during an experiment on neuromodulation in rats. Rats were placed in six different groups, each group to be stimulated with specific pulse frequency. The six groups included a control group that received no stimulation and groups that received stimulation having pulse frequencies of about 0.1 Hz, about 1 Hz, about 10 Hz, about 25 Hz, and about 100 Hz. Pulse width was about 1.0 milliseconds, amplitude was about 15 volts, and stimulation continued for about 3 minutes in duration. Stimulation was applied to the 51 rat nerve, which may correspond to the S2 or S3 nerve in humans.

Graph 180 includes the results of the experiment of FIG. 9. The amplitudes of each sensed cortical evoked potential were normalized to the initial amplitude value of the group. Therefore, graph 180 includes the percent of the initial value for the cortical evoked potentials versus time. Line 182A represents the control group, line 182B represents the subjects that received electrical stimulation having a pulse frequency of about 0.1 Hz, line 182C represents the subjects that received electrical stimulation having a pulse frequency of about 1 Hz, line 182D represents the subjects that received electrical stimulation having a pulse frequency of about 10 Hz, line 182E represents the subjects that received electrical stimulation having a pulse frequency of about 25 Hz, and line 182F represents the subjects that received electrical stimulation having a pulse frequency of about 100 Hz.

As shown in graph 180, the highest potentiation (e.g., amplitude) from the sensed cortical evoked potentials was found in lines 182C and 182D of the 1 Hz and 10 Hz groups, respectively, with an increase of approximately 120% after about 20 minutes from the initiation of electrical stimulation. The results of the experiment indicate that the 1 Hz and 10 Hz groups may benefit the most from electrical stimulation therapy. Lines 182B and 182E of the 0.1 Hz and 25 Hz groups showed a lower amount of potentiation of approximately 50% after 10 minutes. The 100 Hz group did not provide any increase in potentiation.

As can be seen from graph 180, the increase in potentiation occurred relatively quickly within about 10 to 20 minutes. In addition, once the potentiation increased, no decrease in potentiation was observed for the duration of the experiment (e.g., over 70 minutes). Graph 180 indicates that pulse frequencies between approximately 1 Hz and 10 Hz may provide efficacious therapy and that cortical evoked potentials resulting from such electrical stimulation may occur quickly and be relatively long lasting.

Figure 10:
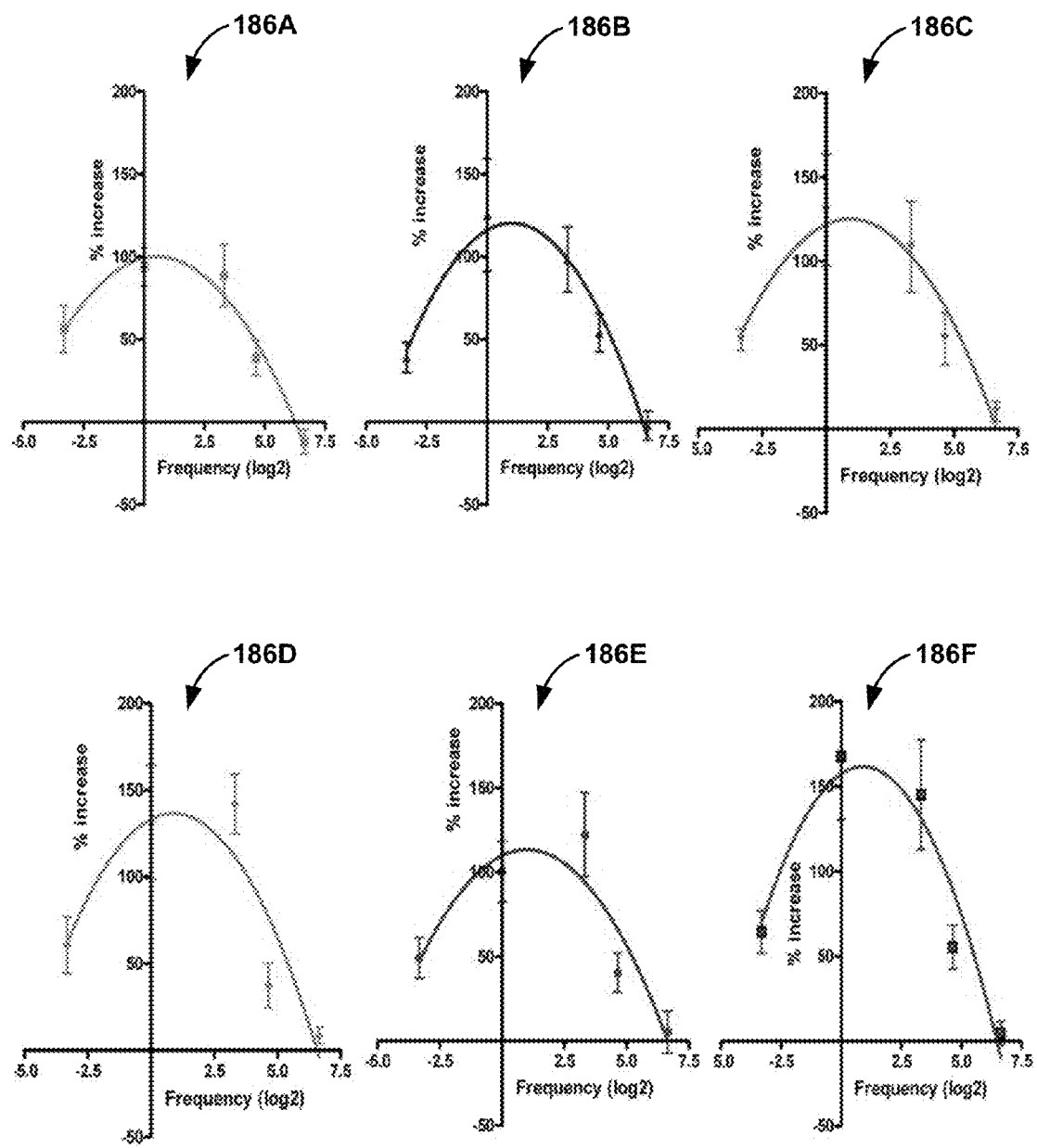
FIG. 10 illustrates example plots of pulse frequency versus normalized increases in amplitude of amplitude of sensed cortical evoked potentials at different time points after initial stimulation.

FIG. 10 is a graph illustrating example plots of pulse frequency versus normalized increases in amplitude of sensed cortical evoked potentials at different time points after initial stimulation. FIG. 10 provides graphs 186A-186F (collectively "graphs 186") of the same data presented in FIG. 9. However, graphs 186 indicate how the increases in potentiation change with frequency of pulses for each duration of time from beginning of stimulation. Graphs 186A, 186B, 186C, 186D, 186E, and 186F provide the frequency of electrical stimulation versus potentiation for 10 minutes, 20 minutes, 30 minutes, 40 minutes, 50 minutes, and 60 minutes from the beginning of therapy, respectively. \

Each of graphs 186 resulted in quadratic curves due to plotting the Log 2 of the frequency. The peak of the curves indicates the frequency for which the greatest increase in cortical evoked potentials occurred. The average peak frequency for all times of graphs 186 was approximately 1.98 Hz. At a frequency of 1.98 Hz, the increase in amplitude of the cortical evoked potentials (relative to a baseline) was approximately 130%. The peak frequency for each of graphs 186A, 186B, 186C, 186D, 186E, and 186F were 1.44 Hz, 2.01 Hz, 2.14 Hz, 1.85 Hz, 2.00 Hz, and 1.87 Hz, respectively. Previously used clinician pulse frequency of approximately 14 Hz only indicates a predicted increase of about 90%. Therefore, the data shown in FIG. 10 indicates that slower frequencies of approximately between about 1 Hz and 3 Hz may provide for effective stimulation therapy.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to monitoring device 40, stimulator 34, IMD 54, and programmer 52, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 52 and IMD 54. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as one or more storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
    receiving a first sensed cortical evoked potential of a patient that occurred in response to a sensation induced at an anatomical region of the patient different from a brain region of the patient;
    receiving a second sensed cortical evoked potential that occurred in response to electrical stimulation delivered to one or more nerves that innervate the anatomical region, wherein the electrical stimulation is at least partially defined by a set of therapy parameter values;
    comparing, by one or more processors, a first value of a characteristic of the first sensed cortical evoked potential to a second value of the characteristic of the second sensed cortical evoked potential; determining, based on the comparison and by the one or more processors, efficacy of a therapy configured to treat a condition associated with the anatomical region; and controlling, based on the determination and by the one or more processors, delivery of the therapy to the one or more nerves that innervate the anatomical region.

2. The method of claim 1, further comprising:
    controlling a sensing system to sense, from the brain region of the patient, the first cortical evoked potential occurring in response to the sensation induced at the anatomical region;
    controlling a medical device to deliver the electrical stimulation to the one or more nerves that innervate the anatomical region; and
    controlling the sensing system to sense, in response to controlling delivery of the electrical stimulation, the second cortical evoked potential from the brain region of the patient.

3. The method of claim 2, wherein controlling the sensing system to sense the first and second cortical evoked potentials comprises controlling the sensing system to sense the first and second cortical evoked potentials via one of electroencephalography, magenetoencephalography, functional magnetic resonance imaging, positron emission tomography, or direct recording by electrodes.

4. The method of claim 1, wherein determining efficacy of the therapy comprises indicating the therapy will be effective in response to determining that a difference between the first and second values of the characteristic is greater than an efficacy threshold.

5. The method of claim 1, wherein the set of therapy parameter values is one set of a plurality of sets of therapy parameter values, and wherein the method further comprises:
    for each set of the plurality of sets of therapy parameter values, controlling delivery of electrical stimulation at least partially defined by the respective set of therapy parameter values;
    responsive to the delivery of electrical stimulation defined by each of the respective sets of therapy parameter values, sensing a respective cortical evoked potential from the brain region of the patient;
    for each of the respective cortical evoked potentials, comparing a respective value of the characteristic of the cortical evoked potential to the first value of the characteristic of the first sensed cortical evoked potential;
    determining, based on the comparisons of the values of the characteristic of the respective cortical evoked potential to the first value of the characteristic of the first sensed cortical evoked potential, the cortical evoked potential with the value of the characteristic having a greatest difference from the first value of the characteristic of the first sensed cortical evoked potential; and
    selecting, for electrical stimulation therapy, the set of therapy parameter values for which the determined respective cortical evoked potential was sensed.

6. The method of claim 1, wherein the characteristic is one of an amplitude of the evoked potential, a duration of the evoked potential, or a latency between stimulation delivery and the evoked potential.

7. The method of claim 1, wherein the set of therapy parameter values comprises a pulse frequency, and wherein the pulse frequency is selected from a range between 0.1 Hertz (Hz) and 25 Hz.

8. The method of claim 1, wherein the therapy is the electrical stimulation defined by the set of therapy parameter values, and wherein the method further comprises delivering, by an implantable medical device, the electrical stimulation to the one or more nerves that innervate the anatomical region.

9. The method of claim 1, wherein the therapy is a pharmaceutical therapy.

10. The method of claim 1, wherein the one or more nerves comprise one of a second sacral nerve or a third sacral nerve.

11. The method of claim 1, wherein the condition is fecal incontinence and the anatomical region is the rectum.

12. A system comprising:
one or more processors configured to:
receive a first sensed cortical evoked potential of a patient that occurred in response to a sensation induced at an anatomical region of the patient different from a brain region of the patient;
receive a second sensed cortical evoked potential that occurred in response to electrical stimulation delivered to one or more nerves that innervate the anatomical region, wherein the electrical stimulation is at least partially defined by a set of therapy parameter values;
compare a first value of a characteristic of the first sensed cortical evoked potential to a second value of the characteristic of the second sensed cortical evoked potential; determine, based on the comparison, efficacy of a therapy configured to treat a condition associated with the anatomical region; and control, based on the determination, delivery of the therapy to the one or more nerves that innervate the anatomical region.

13. The system of claim 12, further comprising:
a therapy delivery module configured to deliver the electrical stimulation to the one or more nerves that innervate the anatomical region; and
a sensing system configured to:
sense, from the brain region of the patient, the first cortical evoked potential occurring in response to the induced sensation at the anatomical region; and
sense the second cortical evoked potential from the brain region of the patient.

14. The system of claim 13, wherein the sensing system is configured to sense the first and second cortical evoked potentials via one of electroencephalography, magenetoencephalography, functional magnetic resonance imaging, positron emission tomography, or direct recording by electrodes.

15. The system of claim 12, wherein the one or more processors are configured to:
determine that a difference between the first and second values of the characteristic is greater than an efficacy threshold; and responsive to the determination, indicate the therapy will be effective.

16. The system of claim 12, wherein the set of therapy parameter values is one set of a plurality of sets of therapy parameter values, and wherein the system further comprises:
a therapy control module configured to, for each set of the plurality of sets of therapy parameter values, control delivery of electrical stimulation at least partially defined by the respective set of therapy parameter values; and
a sensing system configured to, responsive to the delivery of electrical stimulation defined by each of the respective sets of therapy parameter values, sense a respective cortical evoked potential from the brain region of the patient, wherein the one or more processors are configured to:
for each of the respective cortical evoked potentials, compare a respective value of the characteristic of the cortical evoked potential to the first value of the characteristic of the first sensed cortical evoked potential;
determine, based on the comparisons of the values of the characteristic of the respective cortical evoked potential to the first value of the characteristic of the first sensed cortical evoked potential, the cortical evoked potential with the value of the characteristic having a greatest difference from the first value of the characteristic of the first sensed cortical evoked potential; and
select, for electrical stimulation therapy, the set of therapy parameter values for which the determined cortical evoked potential was sensed.

17. The system of claim 12, wherein the characteristic comprises one of an amplitude of the evoked potential, a duration of the evoked potential, and or a latency between stimulation delivery and the evoked potential.

18. The system of claim 12, wherein the set of therapy parameter values comprises a pulse frequency, and wherein the pulse frequency is selected from a range between 0.1 Hz and 25 Hz.

19. The system of claim 12, wherein the therapy is the electrical stimulation defined by the set of therapy parameter values, and the system further comprising an implantable medical device configured to deliver the electrical stimulation to the one or more nerves that innervate the anatomical region.

20. The system of claim 12, wherein the one or more nerves comprise one of a second sacral nerve or a third sacral nerve.

21. The system of claim 12, wherein the condition is fecal incontinence and the anatomical region is the rectum.

22. A system comprising:
means for receiving a first sensed cortical evoked potential of a patient that occurred in response to a sensation induced at an anatomical region of the patient different from a brain region of the patient;
means for receiving a second sensed cortical evoked potential that occurred in response to electrical stimulation delivered to one or more nerves that innervate the anatomical region, wherein the electrical stimulation is at least partially defined by a set of therapy parameter values;
means for comparing a first value of a characteristic of the first sensed cortical evoked potential to a second value of the characteristic of the second sensed cortical evoked potential; means for determining, based on the comparison, efficacy of a therapy configured to treat a condition associated with the anatomical region; and means for controlling, based on the determination, delivery of the therapy to the one or more nerves that innervate the anatomical region.

23. A non-transitory computer-readable storage medium comprising instructions that, when executed by one or more processors, causes the one or more processors to:
receive a first sensed cortical evoked potential of a patient that occurred in response to a sensation induced at an anatomical region of the patient different from a brain region of the patient;
receive a second sensed cortical evoked potential that occurred in response to electrical stimulation delivered to one or more nerves that innervate the anatomical region, wherein the electrical stimulation is at least partially defined by a set of therapy parameter values;
compare a first value of a characteristic of the first sensed cortical evoked potential to a second value of the characteristic of the second sensed cortical evoked potential; determine, based on the comparison, efficacy or a therapy configured to treat a condition associated with the anatomical region; and control, based on the determination, delivery of the therapy to the one or more nerves that innervate the anatomical region.

* * * * *

UNITED STATES PATENT AND TRADEMARK OFFICE
CERTIFICATE OF CORRECTION

| | | |
|---|---|---|
| PATENT NO. | : 9,707,396 B2 | Page 1 of 1 |
| APPLICATION NO. | : 14/063919 | |
| DATED | : July 18, 2017 | |
| INVENTOR(S) | : Su et al. | |

It is certified that error appears in the above-identified patent and that said Letters Patent is hereby corrected as shown below:

In the Claims

Column 27, Claim 13, Line 29: "induced sensation" should read --sensation induced--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*